US012571008B2

(12) United States Patent
Rodrigo et al.

(10) Patent No.: US 12,571,008 B2
(45) Date of Patent: Mar. 10, 2026

(54) METHOD TO PRODUCE A SYNTHESIS PRODUCT, E.G. METHANE UTILIZING METHANOGENIC MICROORGANISMS IN A MICROBIAL ELECTROLYSIS CELL (MEC) BY APPLYING A SEPARATED NUTRIENT FEEDING STRATEGY

(71) Applicant: Electrochaea GmbH, Planegg (DE)

(72) Inventors: Jose Rodrigo, Munich (DE); Nitant Patel, Stockdorf (DE); Matteo Cociancich, Munich (DE); Doris Hafenbradl, Pullach (DE)

(73) Assignee: Electrochaea GmbH, Planegg (DE)

( * ) Notice: Subject to any disclaimer, the term of this patent is extended or adjusted under 35 U.S.C. 154(b) by 380 days.

(21) Appl. No.: 18/024,614

(22) PCT Filed: Aug. 31, 2021

(86) PCT No.: PCT/EP2021/074025
§ 371 (c)(1),
(2) Date: Mar. 3, 2023

(87) PCT Pub. No.: WO2022/049074
PCT Pub. Date: Mar. 10, 2022

(65) Prior Publication Data
US 2023/0399664 A1 Dec. 14, 2023

(30) Foreign Application Priority Data
Sep. 4, 2020 (DE) ..................... 10 2020 123 184.9

(51) Int. Cl.
*C12P 5/02* (2006.01)
(52) U.S. Cl.
CPC ................................... *C12P 5/023* (2013.01)

(58) Field of Classification Search
CPC .. C12P 5/023; C12P 5/007; C12P 7/04; C12P 23/00; C12P 33/00; Y02E 50/30
See application file for complete search history.

(56) References Cited

U.S. PATENT DOCUMENTS

| | | | | |
|---|---|---|---|---|
| 9,428,745 | B2 * | 8/2016 | Mets ..................... | C12N 15/01 |
| 10,533,192 | B2 * | 1/2020 | Buan Murphy ........ | C12P 5/007 |

FOREIGN PATENT DOCUMENTS

| | | |
|---|---|---|
| CN | 109022495 A | 12/2018 |
| CN | 110284150 A | 9/2019 |
| WO | WO-2020089181 A1 | 5/2020 |

OTHER PUBLICATIONS

Lim et al., Effects of applied potential and reactants to hydrogen-producing cathode in a microbial electrolysis cell. Frontiers Chem., 2018, vol. 6, Article 318: pp. 1-19. (Year: 2018).*
Jiang et al., "Removal of Sulfide and Production of Methane from Carbon Dioxide in Microbial Fuel Cells-Microbial Electrolysis Cell (MFCs-MEC) Coupled System", Appl Biochem Biotechnol. 172(5): 2720-2731 (2014).
Luo et al., "Assistant role of bioelectrode on methanogenic reactor under ammonia stress", Bioresource Technology. 217: 72-81 (2016).

* cited by examiner

*Primary Examiner* — Ganapathirama Raghu
(74) *Attorney, Agent, or Firm* — Clark & Elbing LLP

(57) ABSTRACT

The present invention refers to a method to produce methane or at least one other synthesis product by methanogenic microorganisms in a microbial electrolysis cell (MEC), while applying a separated nutrient feeding supply in a discrete or a continuous manner.

24 Claims, 6 Drawing Sheets

Figure 1:
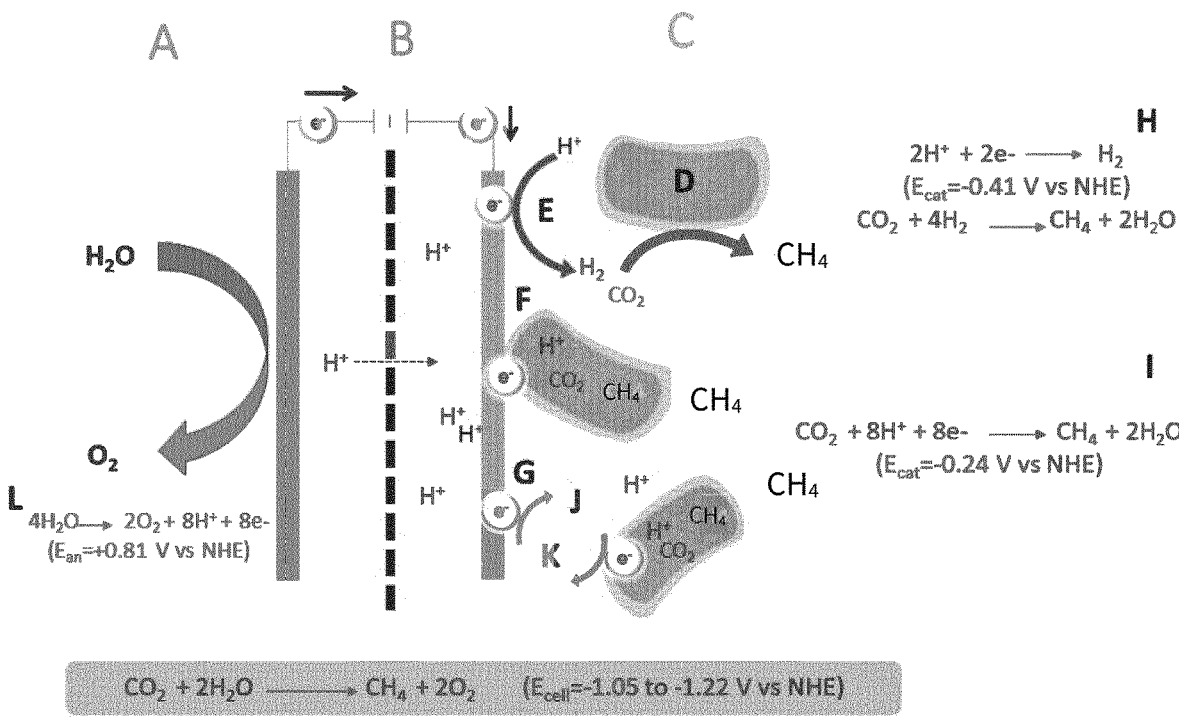

METHOD TO PRODUCE A SYNTHESIS PRODUCT, E.G. METHANE UTILIZING METHANOGENIC MICROORGANISMS IN A MICROBIAL ELECTROLYSIS CELL (MEC) BY APPLYING A SEPARATED NUTRIENT FEEDING STRATEGY

The present invention refers to a method to produce methane during the methane production phase or at least another synthesis product by methanogenic microorganisms from at least one inorganic carbon source in a microbial electrolysis cell (MEC) by involving an improved separated nutrient feeding strategy.

Parts of the project that led to the present patent application were funded by the "Zentrales Innovationsprogramm Mittelstand (ZIM)" of the German Federal Ministry for Economic Affairs and Energy (BMWi) under the reference number 16KN066610.

Methane has the highest energy density per carbon atom among fossil fuels and its potential for energy conversion is far greater than any other natural gas, obtained directly by combustion in presence of oxygen or using fuel cells to produce electricity. Methane's potential for energy generation has become increasingly relevant in the global market.

As natural gas, therefore, methane constitutes a sustainable and renewable energy source and already today increasingly substitutes coal and other fossil fuels.

Recent research has therefore focused on the development and improvement of methods for producing methane with methanogens, e.g. Archaea, which are capable of producing methane from carbon dioxide and hydrogen very efficiently, or which are capable of producing methane in microbial electrolysis cells from a carbon source and input of electrical energy. Presently, the state of the art describes several attempts to enrich gas compositions with methane produced by employing methanogenic microorganisms. For industrial production of methane using Archaea, e.g., *Methanothermobacter thermautotrophicus* strain UC 120910 (ECH100 or ECH0100)—deposited and commercially available may regularly be used.

Upgrading biomethane production to an established scalable and reliable renewable energy source proves to remain a challenge, especially owing to the requirement for a continuous process.

The current invention is based on microbial electrochemical technology (MET) devoted to bio-electromethanation. This process is realized in a microbial electrolysis cell (MEC), which is a unique system capable of converting chemical energy into electrical energy (and vice-versa) while employing microbes as catalysts. The system achieves the combination of electrolysis and methane production in one single reactor, the MEC. Within the MEC, the methanogenic microorganisms reside e.g. at the cathode ("biocathode"). The reactor may comprise a single compartment, or the cathodic compartment, or chamber, may be separated from the anodic compartment, or chamber, e.g. via a semipermeable membrane. In some embodiments of the state of the art, methanogenesis by the methanogenic microorganisms (methanogens, archea) takes place directly in the (bio)cathode compartment, while the electron flow required for the cathodic reduction of classical $CO_2$ to methane is formed in the anode compartment by water oxidation (cf. FIG. 1).

In more detail, within this process, electrical power is used to enhance the potential difference between the anode and the cathode of MEC to enable the bio-electromethanation reaction.

At the cathode a culture of methanogenic microorganisms e.g. using hydrogen may catalyse the methanation reaction as follows:

$$CO_2+4H_2 \rightarrow CH_4+2H_2O \qquad \text{(equation 1)}$$

or $$CO_2+8H^++8e^- \rightarrow CH_4+2H_2O \qquad \text{(equation 2)}$$

or the culture may also catalyse the methanation reaction via an intermediated redox mediator (cf. FIG. 1, bottom).

The water produced by this methanation process (see e.g. equations 1 and 2) is also called "metabolic water" or "free water". A problem associated with the production of metabolic water is the dilution factor of the medium components within the culture medium (catholyte part of electrolytes) that must be specifically addressed. This dilution factor is modified by the liquid migration processes that take place between the anodic and the cathodic chamber which may be separated classically by a proton exchange membrane. The nutrient requirements of the methanogenic organisms are typically supplied as culture medium or as concentrated medium stock solutions in the prior art, which have to be added continuously in continuous or fed batch modes to guarantee a normal methanation rate during operation. This continuous addition of fresh medium stock is a significant detrimental part of the operational costs of the process. Additionally, this state of the art feeding strategy does not specifically meet the actual microbial nutrient requirements that the microorganisms face in MEC as the bio-electromethanation process at the cathode imposes specific nutrient requirements. Moreover, special strains of methanogenic microorgansims also have special and different needs with regards to nutrient usage. One way to face this problem in the state of the art is to supply cell culture media compositions differently formulated with respect to nutrients and nutrients amounts to fulfil the needs of specific strains.

It is thus an object of the present invention to overcome the described disadvantages of the state of the art, especially to situation-adequately optimize the bio-electrochemical processes under continuous operation conditions underlying the bio-electromethanation process and thus to provide a scalable, reliable and continuous production process for methane enriched gas compositions.

The object of the present application has been solved by the newly developed method as specified in claim 1 of the present invention.

In particular, to achieve the stated aim a method is provided to produce methane during the methane production phase and/or at least one other synthesis product by methanogenic microorganisms in a microbial electrolysis cell (MEC), the method comprising the steps:

i. providing a MEC, comprising an anode, a cathode and a culture of methanogenic microorganisms in a suitable liquid aqueous electrolytic culture medium;

ii. culturing the methanogenic microorganisms in a continuous process;

iii. supplying electrons from the anode to the cathode of the MEC and contacting the methanogenic microorganisms with said electrons;

iv. contacting the methanogenic microorganisms with a at least one inorganic carbon source;

v. contacting the methanogenic microorganisms with a nitrogen source and/or a sulfur source by separately supplying the nitrogen source and/or the sulfur source in a discrete or a continuous manner into the culture medium;

vi. collecting methane, a methane enriched gas composition and/or at least one other synthesis product from the MEC.

The method provides improved methane production during a continuous operating process during a methane production phase, after a cell growth phase. The continuous operating process may comprise supply of the nitrogen source and/or the sulfur source in a discrete manner or in a continuous manner.

According to another embodiment of the invention a method is provided to produce and collect a synthesis product other than methane. According to a further embodiment a method is provided to produce methane and at least one other synthesis product and then to separately collect methane, a methane enriched gas composition and the at least other synthesis product from the MEC.

The nitrogen source and the sulfur source may each supplied in a discrete manner timewise separated of each other for example, pulsed within 24 hours of each other. The nitrogen source and the sulfur source may alternatively each supplied in a discrete manner at same time points or overlapping time points, i.e. in a simultaneous manner. Supplying the nitrogen source and the sulfur source in a simultaneous manner can be performed by providing each the sulfur source and the nitrogen source as separate stock solutions and supplying both, e.g. at least at some points by separate supplying means to the culture medium. Alternatively, the sulfur source and the nitrogen source may be already premixed together as at least one to multiple different stock mix solutions with a certain individual stock concentration of the nitrogen source and the sulfur source each. Such a specific stock mix solution may then be supplied as needed by a supplying mean to the culture medium.

The remaining separated electrolytic culture medium, comprising vitamins, non-toxic salt ions and other nutrients necessary for cell growth, may be supplied in a discrete manner or in a continuous manner, preferably in a continuous manner, as long as it is supplied separately from the nitrogen source and/or the sulfur source. The inorganic carbon source is also preferably supplied separately but may be supplied as part of the separated culture medium.

The inventors of the present invention have advantageously and surprisingly found by running a MEC under such separated supply regime (nitrogen source, sulfur source, inorganic carbon source) that this increases the overall efficiency of the system. The overall efficiency of the system was observed to be 30% or higher or preferably to be 50% or higher than in comparable experiments where a standard whole culture medium supply strategy was applied. Processes, which may be included in the calculation of this efficacy are the reduction of costs, saving of nutrients while increasing the overall methanation rate.

For example, efficiencies of 30 $gCH_4/kWh$ can be achieved.

Moreover, the separated supply of nutrients, importantly of the nitrogen source and/or the sulfur source and the at least one inorganic carbon source has the advantage of acting on different variables of the methanation process independently. Thus, in some embodiments, each of the at least one inorganic carbon source, the nitrogen source and/or the sulfur source are supplied separately into the culture medium. These feeding strategies disclosed herein provide beneficial flexibility in terms of process operation with the key goal of maximizing methanogenesis, i.e. energy production in form of methane. With respect to energy recovery in an MFC, high coulombic efficiency is to be targeted. According to the present invention the "coulombic efficiency" expresses the number of electrons that ends ideally in the desired methane produced by electro-methanation. By the separated feeding strategy of the sulfur source and the nitrogen source together with the separated supply of the inorganic carbon source, wherein each of the three nutrients is supplied in a need-dependent/situation-dependent manner according to the method of the present invention the inventors could for the first time truly adapt the supply of (these) nutrients to the needs of the biocatalyst with respect to the availability of electrons in a MEC system. By this the coulombic efficiency of the system was observed to be 30% or higher, 50% or higher or preferably to be 60% or higher than in comparable experiments where a standard whole culture medium supply strategy was applied.

An advantage associated with the present method to produce and collect methane is to save chemicals and connected cost to maintain the methanation process and avoid wasted amounts of chemicals not needed in the process.

According to the present invention a "phase" in the sense of the invention describes a condition or state of the methanogenic microorganisms in the bioreactor of the invention, which is characterized by specific fermentation conditions, which are applied to the methanogenic microorganism, e.g., the ratio of the partial pressures of hydrogen and carbon dioxide or a specific value or range of at least one nutrient, which is applied, e.g. ammonium and/or the settings of the bioreactor to keep cells in the reactor (cell retention) or not.

A "cell growth phase" according to the present invention is a phase mainly characterized by an increase of the biomass of the methanogenic microorganisms by cell division and cell growth. A "methane production phase" according to the present invention is a phase mainly characterized by methane production rather than cell division and cell growth. However, during any cell growth phase, the cells may also or may not produce methane and during any methane production phase, the overall biomass may also increase.

When the microorganisms are in an operating state, the methanogenic microorganisms may be in one of a variety of metabolic phases, which differ with regard to the methanation rate and the division rate and growth rate of the microorganisms, the latter, which can be expressed, as doubling time of microorganism number (division rate) or cell mass (growth rate). The phases typically observed include a lag phase, an active growth phase (also known as exponential or logarithmic phase when microorganisms multiply rapidly), a stationary phase, and a death phase (exponential or logarithmic decline in cell numbers). In some embodiments, the microorganisms of the disclosure are in a lag phase, an active growth phase, a stationary phase, or a nearly stationary phase. The stationary phase is generally the main methane production phase.

The method of the present invention does comprise a step of culturing methanogenic archaea, which is based on typical culture conditions for archaea, which have been previously described and which are known to the practitioner. Such conditions are influenced and controlled—according to the skills of a practitioner by common parameters affecting the culture including temperature, pressure, volume, salt ion content, conductivity, carbon content, nitrogen content, vitamin content, amino acid content, mineral content, or any combination thereof may be varied and are encompassed by the method of the present invention.

The present invention can be performed under so called "cell retention conditions" as described in the international application PCT/EP2020/060979 to avoid—as this widely happens in classical culturing methods of the prior art—that substantial numbers of cells are continuously washed out of the reaction vessel. These washed out cells have to be replaced by further cycles of cell division and cell growth therefore by utilization of $CO_2$ and $H_2$ for the generation and growth of cells rather than for the generation of the aimed methane output. This is unfavourable for the efficiency of the system. Alternatively, and/or additionally there may be the option to supply a sufficient amount of new methanogenic microorganisms to compensate the amount of cells washed out if the MEC is running under no cell-retention conditions (see PCT/EP2020/060979).

The inventors of the present invention have advantageously and surprisingly found out that a separate feeding strategy of either a nitrogen source or a sulfur source or of both improves methane production efficiency and each separately supplied advantageously meet the physiological needs of a respective methanogenic microorganism on a strain dependent manner.

Figure 2:
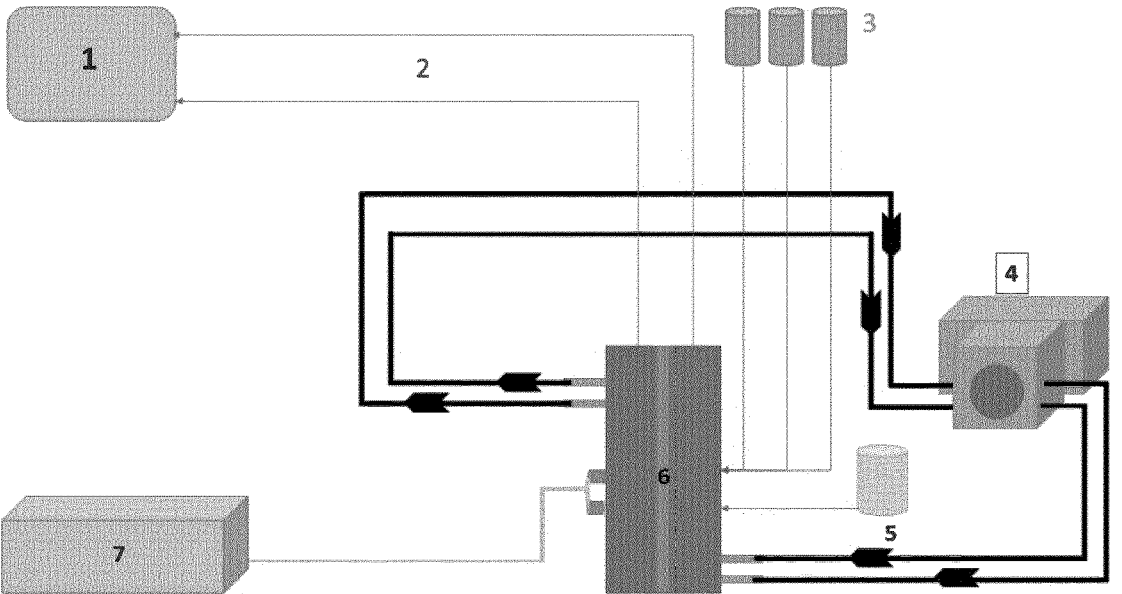

By "feeding in a discrete manner" according to the present invention is meant that the nitrogen source and/or the sulfur source supply will be done discontinuously at certain time points e.g. as a single pulse or a multiplicity of pulses and may be performed according to the concrete and specific demands of the methanogenic microorganism strain. A possible system for the separate feeding strategy of the nitrogen source and/or the sulfur source in a discrete or continuous manner is depicted in FIG. 2 and represented with the letter A-B and C. The Figure also represents the inorganic carbon source applied to the cathode chamber, the pump driving the recirculation of the anolyte and the catholyte, the potentiostat-power source to establish a potential difference between anode and cathode, and the Micro-GC for quality measurements of the out-product gas.

In the context of the present application, "methanation", or "methanogenesis" or "bio-(electro)methanation", is understood as the production of methane or a methane enriched gas composition as carried out by methanogenic microorganisms, such as those included in a list of methanogenic microorganisms suitable to carry out the present invention as described below.

According to the present invention, methanogenic microorganisms are cultured in a microbial electrolysis cell (MEC) in order to produce one or more synthesis products, preferably biomethane. In the context of the present application, steps are regularly disclosed concerning the production of methane without always explicitly adding that they are regularly also concerning the production of the at least one synthesis product different from methane.

Various suitable MECs are known in the state of the art and known by the practitioner. In more detail the microorganisms are cultured in a chamber at the cathode comprised in the MEC. In the understanding of the present invention, a "MEC" stands for a bioreactor, and is either a bioreaction vessel, or a bioreaction enclosure, or a bioreaction tank, and/or at least a bioreaction chamber, and/or a cell, or a combination thereof, as also intended in the state of the art. The MEC may comprise a single compartment, or the cathodic compartment, or chamber, may be separated from the anodic compartment, or chamber, e.g. via a semipermeable membrane. The MEC has to be able to withstand variations of e.g. temperature and/or pressure, among others, and/or able to maintain whichever imparted values of e.g. temperature, and/or pressure are assigned or have to be maintained, before, after or during the reaction process, and wherein the intended reactions relevant for carrying out the invention may take place. Such reactions are understood as bioreactions as they pertain to the domain of reactions wherein microorganisms are involved, and herein referring to their normal physiology—such as e.g. metabolic fermentation, or aerobic or anaerobic digestion—and that, as such, require suitable environments, suitable cultures of microorganisms, suitable culture mediums and suitable reactants to occur. A MEC in the meaning of the invention, performs reliably within the tolerance values of each variable in order to enable the method as disclosed, and it is expected to allow the listed steps to be carried out reliably over time.

A MEC may comprise one or more sensors or components that measure and/or regulate values of, for example, (a) temperature, (b) pressure and/or (c) electrical potential difference, within a pre-set range. The values may be measured and/or regulated before, after or during the reaction process (e.g. methane production).

Cultured methanogenic microorganisms according to the present invention, or autotrophic methanogenic microorganisms may be anaerobic archaea or even recently classified aerotolerant archaea, either in pure strains, or in consortia with a plurality of, i.e. two or more, strains, or in mixed cultures wherein methanation may be also encouraged by syntrophic exchange across different species.

As used herein, the term "methanogenic" refers to microorganisms that produce methane as a metabolic byproduct.

The term "culture" as used herein refers to a population of living microorganisms in or on culture medium. When part of the MEC, the culture medium also serves as the electrolytic medium facilitating electrical conduction within the MEC.

According to the present invention, the method herein disclosed is concerned with the culturing of methanogenic microorganisms in a "continuous process", wherein such continuity is understood as continuity in the production of methane or at least another synthesis product by the methanogenic microorganisms (continuous operating process) and continuity in the culture, wherein no step of separating inactive terminal biomass from active members of the colony is required. It is instead encouraged that dead biomaterial is kept in the reactor together with the active members across several stages of growth, as it is found advantageous that said biomass or biomaterial provide further substrate for the active culture, intensifying nutrition availability. Thus, in some embodiments, the methanogenic microorganisms may be but not necessarily cultured with dead biomaterial inside the bioreactor for a certain period of time, at least 24 hours, 2 days, 3 days, 4 days, 1 week, 2 weeks, 3 weeks, 1 month, or more.

In the understanding of such continuity of methane production and culture, or the production of a at least other synthesis product and culture, is also included the understanding that a continuous supply of suitable reactants is given to the culture, allowing it to carry out its methane production task without significant alteration of the measured amount of produced methane (i.e. yield of methane) obtained from any cycle of methanogenic activity across the culture and within the operational phases of the reactor. This supply regime of chemical components applies with the exception that certain reactants most prominent the nitrogen source and the sulfur source can alternatively and at least time wise be supplied either both or only one of them by way of feeding in a discrete manner instead of a continuous manner.

In some embodiments, suitable reactants, other than the separate supply of the nitrogen source and/or the sulfur source, are supplied to the MEC in a continuous or fed batch manner, allowing the methanogenic microorganisms to carry out methane production without significant alteration of the measured amount of produced methane (i.e. yield of methane) obtained from any cycle of methanogenic activity across the culture and within the operational phases of the reactor. In some embodiments, the nitrogen source or the sulfur source or both are supplied by feeding in a discrete manner instead of a continuous manner, while the other reactants are supplied in a continuous manner.

Ensuring a continuous methane production or of the other at least one synthesis product at the envisioned rage of efficiencies is a relevant feature of the present invention and an advantageous effect of implementing the steps of the method as described. According to the invention, methane is produced by methanogenic archaea from single strains or in mixed cultures, wherein a mixed culture is either a culture where a plurality of, therefore two or more, strains may also be employed, or a culture where a plurality of additional species interact with methanogenic archaea, or any combination thereof.

According to an embodiment of the present invention a "refreshing of the culture medium" can be realized by exchanging the cell culture medium at least partly or by adding at least one nutrient, which triggers cell division and cell growth. Nutrients, which trigger cell growth and cell division are well known by an artisan and include the addition or the increase of a nitrogen source, a sulfur source, phosphorous and cell growth factors. A combination of the described options for refreshing of the culture medium is also a possible option according to the present invention. Such a "refreshing of the culture medium" may be but not necessarily be applied every month, every half year for at least one day or at least one day to five days or at least one day to four days at least one day to three days.

According to a further embodiment the MEC comprises at least (a) a first chamber containing the cathode and the culture of the methanogenic microorganism in the culture medium;

(b) a second chamber containing at least the anode;

(c) optionally a proton permeable, gas impermeable barrier between the first chamber and the second chamber; and preferably the nitrogen source and/or the sulfur source are supplied in a discrete manner.

A conductive conduit, connected to a power source, may connect the anode and the cathode such that the power source provides an electrical potential difference between the anode and the cathode. Optionally the MEC comprises a sensor to measure the electrical potential difference between the anode and the cathode, or the oxidative reduction potential. Optionally the MEC further comprises a sensor that measures current density, temperature, or pressure. The MEC may also comprise one or more sensors that measure each the input of separately supplied culture medium, nitrogen source and/or sulfur source.

According to an additional embodiment of the method of the present invention step v. further comprises:

continuously controlling and regulating the concentration of the nitrogen source in the culture medium to maintain the nitrogen source concentration in the culture medium to be at a given amount of 0.005 to 0.2 M or of 0.02 to 0.2 M, preferably between 0.01 to 0.02 M. For this, the nitrogen source is preferably supplied in a discrete manner.

Accordingly, the methanogenic microorganism culture is continuously controlled and regulated, i.e. stabilized to be kept cultured at a nitrogen source concentration at a given amount.

According to an embodiment the nitrogen source is $NH_3$ and the method of the present invention step v. further comprises:

continuously controlling the nitrogen source in the culture medium and regulating said concentration of the nitrogen source, when the nitrogen source concentration in the culture medium is lower than 0.2 M, lower than 0.02 M, lower than 0.01 M or lower than M to maintain the nitrogen source concentration in the culture medium to be at a given amount of 0.2 to 0.005 M or of 0.2 to 0.02 M, preferably between 0.02 to 0.01 M. For this, the nitrogen source is preferably supplied in a discrete manner.

In any of the embodiments disclosed herein, the nitrogen source is supplied at the lowest minimum levels, for example, in a discrete manner or continuous manner. The method may comprise regulating the nitrogen source concentration in the cathode chamber of the MEC to regulate the concentration of nitrogen within a specified range, e.g. a level lower than 0.8 M, or M, or 0.007 M.

Figures 7, 8:
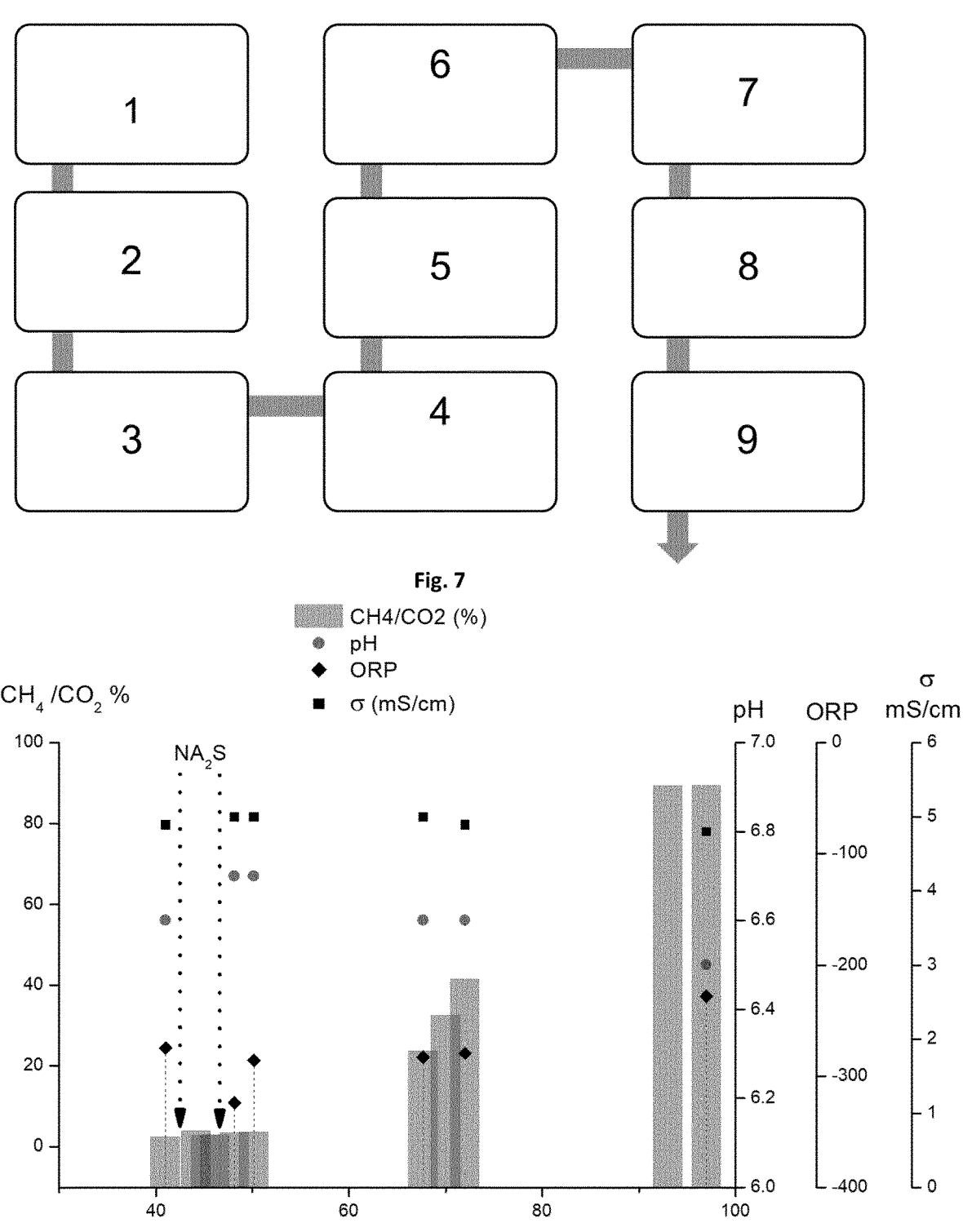

Methanogenic microorganisms generally need a nitrogen source and accordingly all published prior art documents teach the supply of nitrogen in one or the other way. The influence how a nitrogen source pulse or a sulfur source pulse (each discrete supply) influences parameters of the methanation process—without being bound by the theory— as salinity of the culture medium (cathode side), the pH, the current, the $CH_4/CO_2$ conversion, the hydrogen production and the optical density is depicted in FIG. 7.

According to another embodiment of the method of the present invention step v. further comprises:

continuously controlling and regulating the sulfur source concentration in the culture medium to maintain the sulfur source concentration in the culture medium to be at a given amount of 0.1 to 100 mM or of 10 to 80 mM, preferably between 15 to 30 mM and preferably discretely supply the sulfur source.

Accordingly, the methanogenic microorganism culture is continuously controlled and regulated, i.e. stabilized to be kept cultured at a sulfur source concentration at a given amount.

In any of the embodiments disclosed herein, the sulfur source is supplied at the lowest minimum levels necessary, for example, in a discrete manner or continuous manner. The method may comprise regulating the sulfur source concentration in the cathode chamber of the MEC to regulate the concentration of sulfur within a specified range, e.g. a level lower than 100 mM, or lower than 50 mM, or lower than 20 mM or lower than 10 mM.

According to some embodiments of the present invention, the method comprises regulating the sulfur source in dependance to the oxidation-reduction potential (ORP). Thus, according to another embodiment of the method of the present invention step v. further comprises:

continuously controlling the sulfur source concentration in the culture medium and regulating the sulfur source concentration in the culture medium to maintain the sulfur source concentration in the culture medium to be at a given amount of 0.1 to 100 mM or of 10 to 80 mM, preferably between 15 to 30 mM and discretely supply the sulfur source, when the oxidation-reduction potential (ORP) in the culture medium is lower than −200, lower than −350, lower than −400 or lower than −450.

Sulfur may act as a reducing agent to maintain the low oxidation-reduction potential (ORP) in the growth medium that is regarded as important to a productive operating of the methanogenic microorganisms, e.g. for methanogenesis. Additionally, in methanogens is a key element of enzymes catalysing the reactions involved in the $CO_2$ reduction to methane with $H_2$, e.g., as part of the prosthetic groups in the $[4Fe_4S]$-cluster of the $F_{420}$-reducing hydrogenases that catalyse the reversible reaction of coenzyme $F_{420}$ with $H_2$.

According to another embodiment of the method of the present invention step v. further comprises:

continuously controlling and regulating the concentration of the nitrogen source in the culture medium to maintain the nitrogen source concentration in the culture medium to be at a given amount of 0.005 to 0.2 M or of 0.02 to 0.2 M, preferably between 0.01 to 0.02 M. For this, the nitrogen source is preferably supplied in a discrete manner.

continuously controlling and regulating the sulfur source concentration in the culture medium to maintain the sulfur source concentration in the culture medium to be at a given amount of 0.1 to 100 mM or of 10 to 80 mM, preferably between 15 to 30 mM and discretely supply the sulfur source.

For this, the nitrogen source and the sulfur source are preferably supplied in a discrete manner.

According to another embodiment of the method of the present invention step v. further comprises:

continuously controlling the nitrogen source in the culture medium and regulating said concentration of the nitrogen source, when the nitrogen source concentration in the culture medium is lower than 0.2 M, lower than 0.02 M, lower than 0.01 M or lower than M to maintain the nitrogen source concentration in the culture medium to be at a given amount of 0.2 to 0.005 M or of 0.2 to 0.02 M, preferably between 0.02 to 0.01 M. For this, the nitrogen source is preferably supplied in a discrete manner.

continuously controlling the sulfur source concentration in the culture medium and regulating the sulfur source concentration in the culture medium to maintain the sulfur source concentration in the culture medium to be at a given amount of 0.1 to 100 mM or of 10 to 80 mM, preferably between 15 to 30 mM and discretely supply the sulfur source, when the oxidation-reduction potential (ORP) in the culture medium is lower than −200, lower than −350, lower than −400 or lower than −450. For this, the nitrogen source and the sulfur source are preferably supplied in a discrete manner.

According to the present invention the oxidation-reduction potential (ORP) or redox potential is a measure of the tendency of an aqueous solution to either gain or lose electrons when it is subjected to change by introduction of a new chemical species. Methanogens can be generally sensitive towards $O_2$ and can be inhibited or even killed by certain amounts or even traces of oxygen (strain dependently). Therefore, a low ORP, which varies linearly with the logarithm of $O_2$ concentration, helps to maintain their metabolic activity. There are different procedures available in the state of the art to calculate the ORP, well known by a practitioner. The ORP is e.g. determined by measuring the potential of a chemically-inert (platinum) electrode which is immersed in the solution. The sensing electrode potential is read relative to the reference electrode of the pH probe and the value is presented in millivolts (mV). In other words: The potential difference between these electrodes or ORP (mV) is measured by using an ORPmeter. Normally the ORP during a methane production phase according to the present invention is in a range of −450 to −200 mV.

The inventors of the present invention have surprisingly and advantageously found by ways of initial comparative experimentations that providing of the nitrogen source and the sulfur source (e.g. each by means of a pulse (discrete supply)) together but timewise separated from each other, e.g. pulsed within 24 hours of each other or pulsed at same time points or at overlapping time points leading to a higher increase of the $CH_4/CO_2$ conversion rate as compared with providing each the nitrogen source or the sulfur source alone (synergistic effect). Without being bound by that theory the inventors believe that the concomitant providing (at same time points or at overlapping time points) of the nitrogen source and the sulfur source especially by influencing the pH is the reason for this synergistic effect. This positively triggers follow up reactions in the reaction cascade and thus leading to an increase of the $CH_4/CO_2$ conversion as compared with providing each the nitrogen source or the sulfur source alone (see FIG. 7 and FIG. 12). Notably and very promisingly, there was a significant beneficial synergistic increase (over 50%) of the percentage $CO_2$ and $H_2$ conversion to $CH_4$ within 24 hours after punctually pulsing ammonium hydroxide (a total increase of 7.5 mM in the catholyte increasing) and $Na_2S$ (establishing a 1.2 mM increase of the total concentration of this compound in the catholyte) in a simultaneous manner (cf. FIG. 12).

Furthermore, common culture or growth mediums to be provided to the culture of methanogenic organisms may include common inorganic elements, in their elemental forms or in any suitable non-toxic salt ions thereof, e.g. sodium, potassium, magnesium, calcium, iron, chloride, sources of sulfur, e.g. hydrogen sulfide or elemental sulfur, phosphorus sources, e.g. phosphate, nitrogen sources, e.g. ammonium, nitrate or nitrogen gas. The culture medium according to the present invention is supplied separately from the nitrogen source and sulfur source and optionally also separately from the at least one inorganic carbon source. It may comprise other nutrients necessary for cell growth, including vitamins, and non-toxic salt ions, and optionally comprise minimal amounts of sulfur and nitrogen, but preferably omit sulfur and nitrogen.

Typical supplied salts utilized for culturing methanogenic organisms according to the present invention are NaCl, $KH_2PO_4$, $FeCl_2$—$4H_2O$, $Na_2SeO_3$, $Na_2S$, $NH_4OH$ and $MgCl_2$.

The present invention is besides others characterized by a step of controlling the external supply of the nitrogen source and/or the (resulted) concentration of the nitrogen source (e.g. ammonia) within the cell culture medium. Similarly, the present invention is also characterized by a step of controlling the external supply of the sulfur source and/or the (resulted) concentration of the sulfur source (e.g. $Na_2S$) within the cell culture medium. In this context, "controlling" is understood in the general common meaning of keeping under constant monitoring the parameters related to the culture and essentially measuring said parameters or status indicators, using common methodologies and measuring instrumentation known in the art. Since it might not be sufficient to keep under constant monitoring and therefore only control this parameter of the culture; therefore, a further embodiment of the present invention comprises in particular regulating the nitrogen source concentration and/or the sulfur source concentration within the cell culture medium continuously.

In the understanding of the present application, "regulating" is intended as actively maintaining a "given value" or a given value span for a parameter, e.g. the nitrogen source/ sulfur source concentration of the culture, by using appropriate means to do so.

A "given value" according to the invention may be a defined value with given tolerances, tolerances within the measurements system or tolerances due to the variability within the culture or due to the culture diversity, wherein said value is suitable for enabling methanation; or a given value may be a range of suitable values, which achieve the same effect on methanation as a given value.

The inventors of the present invention have surprisingly found that if the nitrogen source and the sulfur source are both controlled and separately supplied in a need-related manner (by discrete or continuous supply) that this feeding regime in particular allows for increased flexibility in terms of needed process operations with the key goal of maximizing methanogenesis, i.e., e.g. energy production in form of methane. Moreover, with a situation- and need-dependent supply of the nitrogen source and the sulfur source the more chemicals and connected cost to maintain the methanation process are saved and associated waste amounts of chemicals not needed in the process are beneficially more reduced as when supplying only one either the nitrogen source or the sulfur source alone.

Figure 3:
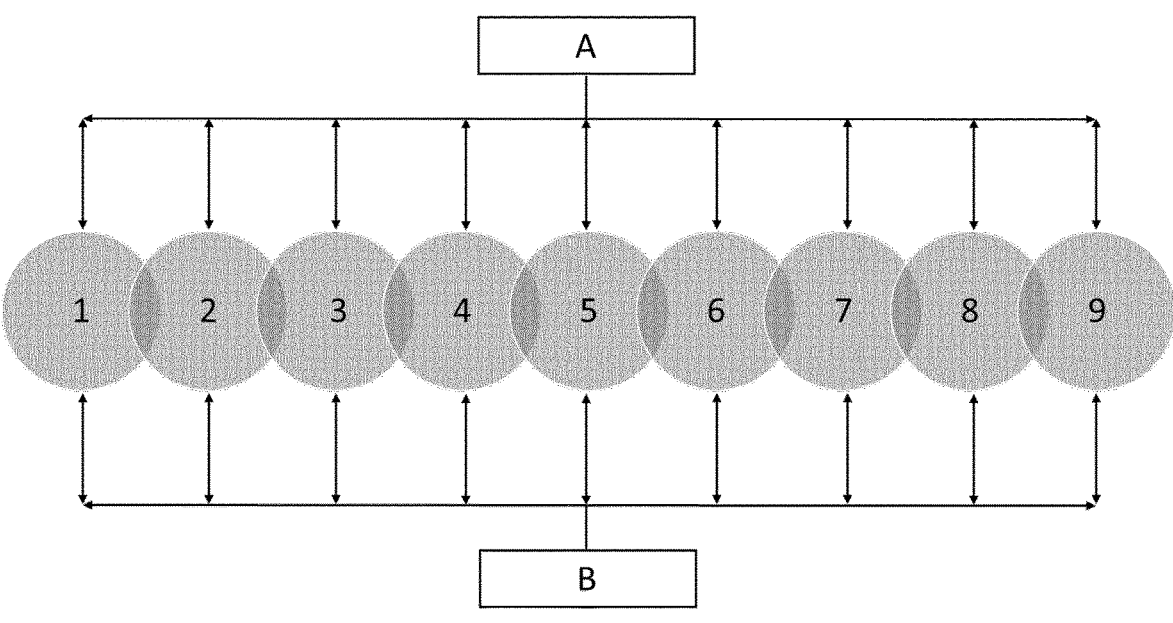

The interrelation of the separated supplied nitrogen source (e.g. $NH_3$) and the sulfur source (e.g. $Na_2S$) in the culture medium can advantageously act situation-dependent on several MEC performance variables, e.g., pH, ORP, cell proliferation, etc. that are at the same time interrelated each other as depicted in FIG. 3. Some of these variables responses are directly connected with the nitrogen source (e.g. pH) and the sulfur source (e.g. ORP) and their change concurrently triggers the variation in a battery of indirect variables, e.g., methanation rate. The rest of the media components (e.g. vitamins, minerals, salt ions etc.) can be supplied together compensating the catholyte dilution factor, i.e., the water formation produced because of the methanation reaction driven by the methanogenic microorganisms (metabolic water) and/or the dilution, which occurs due to the migration of the catholyte and anolyte part of the electrolytes through the membrane.

In some of the embodiments disclosed herein, the method comprises regulating the sulfur source proportionate to the current density or to the projected electrode area. According to a further embodiment the sulfur source is supplied to maintain a ratio of a projected electrode area ($m^2$) to sulfur source concentration in the culture medium (mol/L) in the range of 1:0.1 to 1:10, or 1:1.5 to 1:3, preferably in the range of 1:2 to 1:3 or 1:2 to 1:2.5.

When sulfur is not used as a reducing agent, the amount of sulfur supplied is reduced and the ratio is correspondingly reduced, e.g. to ranges of 1:0.001 to 1:0.1.

According to the present invention "the projected electrode area" is the surface area of an electrode, i.e. the geometrical area. It can be measured by methods of the state of the art as geometric methods well known by the skilled person. These methods use simple mathematical formulas to calculate areas of regular geometrical figures, such as triangles, trapeziums*, or areas bounded by an irregular curve.

According to a further embodiment $H_2O$ is the primary net electron donor for the methanogenic organisms.

In more detail, it is believed—without being bound by the theory—that the separated supply of the nitrogen source and/or the sulfur source allows to act beneficial on the following parameters in a species-dependent and/or a situation-dependent manner:

The Electrolyte pH and on the Strain Optical Density (OD):

The nitrogen source supplied in form of e.g. $NH_3$ can act as a pH regulator balancing acidity created by the dissolution of the inorganic carbon source, e.g. $CO_2$ (as $NH_4OH$) or alkalinity by the $OH^-$ generation (by means of $H_2O$ reduction) at the cathode (as $NH_4^+$). In another embodiment of the present invention the buffering role of the nitrogen source may be combined with an extra buffer, e.g. a phosphate buffer. In such a case, the nitrogen requirement for pH balancing may be lower than for cell growth, wherein the nitrogen source, e.g. $NH_3$ acts as a key nutrient for protein synthesis in archaea. $NH_3$ may be supplied at the cathodic chamber as far as needed to balance pH and maximize methanation, both variable in combination with the lowest OD.

On the Oxidation-Reduction Potential (ORP) Variable and on the Methanation Rate:

The sulfur source, e.g. in form of $Na_2S$ may establish a low ORP, a fundamental requirement to provide the adequate thermodynamic conditions for the methanation reaction. As long the ORP is maintained low enough by $Na_2S$, the concentration of such a compound will be only increased if needed for further synthesis stimulation of the necessary enzymatic components required for methanation, e.g., $[4Fe_4S]$-cluster of the $F_{420}$-reducing hydrogenases that catalyse the reversible reaction of coenzyme $F_{420}$ with $H_2$.

On Adaptation Processes to New Supply of Inorganic Carbon Source, e.g. In Form of $CO_2$ and Electron Flow Scenarios:

The inventors of the present invention found that the necessary compounds needed to act on pH, OD, ORP and methanation rates may be also regulated to adapt to new potential methanation scenarios in terms of the concentration of the inorganic carbon source, e.g. $CO_2$ concentration. These new $CO_2$ scenarios depend on the $CO_2$ influx flow that at the same time depends on the electron flow from the anodic toward the cathodic chamber.

Accordingly, the inventors of the present invention found—without being bound by that theory—that the independent provision of the nitrogen source and/or sulfur source allow for the following actions:

Provision of the optimal concentration of the sulfur source to achieve the adequate initial redox potential for the methanogenic microorganisms. This sulfur source provision must be compatible with initial pH range (e.g. 6 to 11) and with the minimum lag phase for achieving the maximum methanation rate (in terms of the electrons to $CH_4$ ratio)

Stepwise variation of the sulfur source supply to adapt to the different system evolution phases, i.e., lag, exponential and stationary phase in terms of strain proliferation and methanation rate. This variation must be determined on the flow of the inorganic carbon source, e.g. in form of $CO_2$.

Provision of the optimal initial nitrogen source concentration to support the ideal strain growth and to adjust this concentration to the needs of the strain in each of the different process phases including the stationary phase.

Ability to Act Under Different Sub-Optimal Conditions/ Scenarios:

a. Inadequate ORP conditions: Methanogenesis driven by methanogenic microorganisms generally requires a low oxidation-reduction potential (ORP) in a range of around −200 to −450 mV. A suboptimal value of above −250 mV, caused by e.g. an oxygen diffusion to the catholyte may be an event where $Na_2S$ may be supplied. $Na_2S$ may function to reverse the inadequate ORP conditions due to deficient membrane performance (oxygen diffusion through the cathode) by acting as a scavenger agent for oxygen and thereby decreasing the ORP. Provisional oxygen contamination may also occur through other mechanisms as e.g. chemical solution (incomplete anoxic chemical solution), $CO_2$ gas flows or un-tight MEC system's elements.

b. Adjustment of the electron flow in the MEC, i.e., the electron donor at the bio-electromethanation cathodic reaction may react to different variable, e.g., salinity, MEC voltage, temperature, electrolyte composition, etc.

Thus, the oxidation of the electron donor (e.g. $H_2O$) and the resulting electron flow from the anode to the cathode determine the potential flow of the inorganic carbon source (e.g. $CO_2$) that may be converted to methane due to the 8 electrons required for its formation. The variation in this carbon flow supply (externally) influences pH, ORP, cell growth, methanation rate, etc., see e.g. in the following potential exemplary scenarios. The methods provided herein also provide steps to respond and counteract to variations from the desired ranges by controlling and regulating the inorganic carbon source, the nitrogen source and the sulfur source as will be described in the following:

Scenario A: Increased Current→Counter Action: Increasing Inorganic Carbon Source Flow (e.g. $CO_2$Flow)

In the event of an increased current the counter action is to increase the inorganic carbon source flow (e.g. $CO_2$ flow). In this scenario the pH and ORP may vary due to the increase of the $CO_2$ flow. The pH may decrease due to more $CO_2$ in solution (as carbonic acid). The ORP may increase due to more acidic condition that trigger the conversion of present $Na_2S$ to $H_2S$ (the latter, which will leave the system as a gas).

Potential Counter Action:

For ORP: Feeding with the sulfur source (e.g. $Na_2S$) will alkaline the catholyte and will bring down the ORP again.

For pH: Extra buffer/nitrogen source (e.g. ammonia) should be spiked when the ORP is e.g. under −450 mV (as targeted) but the pH is detrimental still under a threshold, e.g. under pH value 6.5.

Scenario B: Decreased Current→Counter Action: Lowering Inorganic Carbon Source Flow (e.g. $CO_2$Flow)

In the event of a decreased current the counter action is to decrease the inorganic carbon sourceflow (e.g. $CO_2$ flow).

Additionally, a pulse of fresh media at the cathode to increase salinity and therefore current production is possible.

If the current remains lower, pH may vary but ORP should stay stable or going towards more negative values.

The pH value may increase due to less $CO_2$ in solution (as carbonic acid).

Potential counter action for pH: Feeding with a pulse of acid (e.g. HCl) to regulate the pH.

Scenario C: Decreased Conversion of the Inorganic Carbon Source (e.g. $CO_2$) to Methane i) if this Scenario is Associated with an Increased $OD_{610}$ During the Last Operation Hours;

Potential counter action: supply growth media (e.g. strain-specific), optional supply nickel and/or the sulfur source (e.g. $Na_2S$) to maximize the synthesis of the enzymatic metabolic components of the strain that may maximize the $CO_2$ to methane conversion, e.g., [$4Fe_4S$]-cluster of the $F_{420}$-reducing hydrogenases that catalyse the reversible reaction of coenzyme $F_{420}$ with $H_2$.

ii) if this Scenario is Associated with a Decreased $OD_{610}$ During the Last Operation Hours;

Potential counter action: supply the nitrogen source as a key component for the protein-biomass ($OD_{610}$ increase) production until the conversion $CO_2$ to methane is maximal regarding the electron to $CO_2$ supply. The ideal scenario may be reached under the maximal conversion rate with the minimum biomass and hence the minimum operational cost in chemicals.

Accordingly, the separated supply of the nitrogen source and/or the sulfur source (e.g. $NH_4OH/Cl$, $Na_2S$) together with the classical separated supply of the inorganic carbon source (e.g. $CO_2$) permits a potential intervention to adjust to the new electron donor and acceptor flows in a need and situation dependent manner to maintain the maximum methanation rate for a specific methanogenic microorganism strain (also for a specific methanogen strain in general).

Thus, in other words: Adapting to new electron donor and acceptor flows scenarios according to the present invention beneficially reduces the times of adaptation of a certain experimental strain culture to these new flows in terms of cell proliferation and growth, pH and ORP stability and methanation rates. The inventors of the present invention surprisingly found out that this separated supply of necessary nutrients has the advantage of acting independently on different variables of the methanation process of a methanogenic microorganism culture to allow for a situation-dependent and strain-dependent optimized methanation rate. Thus, this feeding regime further provides flexibility in terms of operation during the MEC methanation process.

Moreover, in initial experimentations (data not shown) at the start of inoculation of the MEC with the methanogenic microorganisms the inventors increased the initial concentration and the regular dosing of $Na_2S$ (sulfur source) situation-dependent until a stable methanation was reached. They found—without being bound by theory—that by applying such a separated feeding regime at the start of inoculation that this reduces the duration of the lag phase of the metabolic phases of the culture of methanogenic microorganisms. This in turn is beneficial in terms of methane production as the stationary phase (=main methanation phase) begins earlier, thus leading to an earlier higher methanation rate.

Moreover, in these initial experimentations performed the initial and regularly high concentration and further dosing of the nitrogen source could be reduced dependent on the needs of the culture of the used methanogenic microorganism strain.

It is believed—without being bound by that theory—that when the majority of methanogenic microorganisms are kept inside the reactor or the reactor system e.g. including also the pipes of a pump system (as this is the case in the continuous operating system of the present invention), then the growth of the cells is only mainly required in a pronounced amount in the "growth phase" at the beginning of the start-up of a reactor (lag phase) and not during methane production phase. This results in a nitrogen saving for the cells during the methane production phase. However, if a cell population of sufficient number is directly applied in the start-up of the reactor a growth phase is not necessary.

Additionally, it is believed—without being bound by theory—that the reason why the total cell number of the methanogenic microorganisms stays quite stabilized over time even under prolonged reduction of the external supply of the nitrogen source in the methane production phase, is that the nitrogen during natural turn-over of pre-existing cell mass of the methanogenic microorganisms developed in the growth phase is used to build up new cells during the archaea generation cycle in the methane production phase. This would mean that the nutrients of e.g. dying methanogenic microorganisms including nitrogen are recycled by the living methanogenic microorganisms to grow and/or to build up new cells by division. Therefore, nitrogen may only be moderately used situation dependently, i.e. mainly to build up new cells, which disappeared, e.g. which were washed out of the reactor system (when the reactor runs under no-cell retention conditions) or because detrimental conditions in the reactor occur, which lead to a reduction in the number of the cultures of methanogenic microorganisms (measurable e.g. by an reduced value at $OD_{610}$).

According to another embodiment of the present invention step v. further comprises to continuously control and regulate the concentration of at least one other source of inorganic elements in the culture medium in their elemental form or in form of any suitable non-toxic salt ions thereof, e.g. selected from the group consisting of sodium, potassium, magnesium, calcium, iron, chloride or phosphate by a separate supply in a continuous or discrete manner.

According to an additional embodiment the concentration of said at least one other source of inorganic elements in the culture medium may be continuously controlled and regulated to be maintained, i.e. stabilized at a certain given value or range in relation to the methanation rate and/or to the metabolic water production rate. It is done to address/counteract the rate of consumption of the at least one other source of inorganic elements in the culture medium driven by the methanation process and/or to counteract the progressive dilution due to the production of metabolic water. According to an embodiment at least one or all said inorganic elements may be already premixed together as at least one to multiple different stock mix solutions with a certain individual stock concentration of each of the individual different inorganic elements. Such a specific stock mix solution may then be supplied as needed by a supplying mean to the culture medium and optionally in relation to the methanation rate and/or metabolic water production rate or to the rate and amount of removal of diluted cell culture medium from the overall cell culture medium volume to remove excess metabolic water from the system.

This brings (more pronounced than the separated supply of the nitrogen source, the sulfur source and the at least one inorganic carbon source either each alone or combined) the advantage to have a feeding strategy, which even better fulfills the needs of a culture of methanogenic microorganisms in a strain dependent manner without the need of different formulated cell culture media to be continuously supplied.

The inventors of the present invention believe—without being bound by that theory—that the more individual nutrients are separately supplied in a continuous or discrete manner if needed the more increased is the flexibility in terms of process operations with respect to methanogenesis.

According to another embodiment of the present invention the step of culturing the methanogenic organisms further comprise:
   keeping the culture conditions anaerobic or facultatively anaerobic;
   keeping the temperatures in a range from 32° C. and 85° C.;
   carrying out the entire method or at least one step under atmospheric pressure conditions and/or under pressurized conditions with up to 16 or up to 420 bar;

maintaining the methanogenic microorganism density at a range of 0.01-50 g/L, 0.025-0.625 g/L, 0.1 to 0.5 g/L, 3.5-30 g/L, 5-20 g/L or 5-10 g/L.

According to the present invention, the step of culturing the methanogenic organisms further comprise keeping the temperatures in a range between 32° C. and 85° C.; preferably 50-70° C. or 62-67° C.

According to another embodiment of the present invention the step of culturing the methanogenic organisms additionally comprise recirculating the culture, wherein the recirculating of the culture can be carried out regularly, in intervals, continuously, or keeping the soluble culture at least in a certain slow and constant movement.

While the temperatures may vary according to the presence of selected microorganism species within the culture, each of which better thrive within set ranges of temperatures, for most of the methanogenic microorganisms increased temperatures are not detrimental, and they may even assist in optimizing cellular metabolism and thus metabolic turnover or even methanation. In an industrial process a temperature must be controlled by energetic regulation; in this regard it is to be considered a valuable feature to reduce energy expenditure by enabling temperature control.

Consequently, it is of substantial importance to balance the optimized culture temperature and the corresponding hydrogen solubility against the costs for energy input. Interestingly, the method of the present invention was found to be most efficient in a temperature range between 32° C. and 85° C., or alternatively 50 to 70° C. or further alternatively 62-67° C. at atmospheric pressure. If according to some embodiments one or more steps of the method according to the invention are carried out in a pressurized atmosphere, then the pressure is chosen to be preferably up to 16 bar, alternatively up to 20 bar, alternatively up to 50 bar, alternatively up to 68 bar, alternatively up to 110 bar or even up to 420 bar.

For other temperature or pressure ranges hydrogen solubility can be used as comparative feature. Accordingly, the present invention also refers to a culturing process at pressures equal or between the range of 1 to 10 bar. High pressure, e.g. 16 bar, 20 bar, 35 bar, 40 bar or 60 bar and correspondingly, higher temperatures, which would allow the same hydrogen solubility as at a temperature range between 32° C. and 85° C., or alternatively 50 to 70° C. or further alternatively 62-67° C. at atmospheric pressure are also encompassed.

Methanogenic microorganisms, in general, may live and grow also in a plurality of other and even extreme temperature ranges up to and well above 100° C., e.g. 140° C.; accordingly, the above temperature range is an indication of a preferred range, but it is not to be understood as limiting the scope of the invention.

Preferably, according to a further embodiment of the invention the nitrogen source is but not limited to diatomic nitrogen ($N_2$), ammonia ($NH_3$), nitrate or nitrite salt ions, ammonium ($NH_4^+$) compounds, preferably in the form of $NH_4OH$ or $NH_4Cl$ or combinations of the aforementioned. According to an embodiment the nitrogen source is ammonia. According to another embodiment the nitrogen source is an ammonium compound, preferably in the form of $NH_4OH$.

The concentration of living cells in the culture medium (culture density) is in some embodiments maintained above 0.01 g dry weight/L. In certain embodiments, the density may be 50 g dry weight/L or higher.

The $OD_{610}$ (optical density at 610 nm) or briefly optical density of microorganisms in a culture is a viable parameter to measure the cell count or concentration at each time point. In particular the optical density (OD) of the culture according to the present invention is measured utilizing common methods and standards known in the art. Optical density, or, rather, turbidity measurements as a form of cell counting are performed using a spectrophotometer, is typically operated around or at 600 nm, but accordingly other wavelengths may be suitable.

Because the optical density may vary according to the measurement setup, it is often useful to indicate the dry weight or biomass density of the microorganisms in the culture as a measure of the amount of cells present in a culture at a given time point or growth phase. It is possible to establish a correlation between measurements of OD of a given culture at a given growth stage and dry weight by building a curve of a number of different OD values of the culture obtained at different concentrations and measuring the dry weight of the dried sample of culture accordingly, using standard methods known in the art. This will provide a set of data point of dry weight as a function of the optical density; the slope of the regression line of such data set usually defines the correlation between dry weight and optical density. According to the inventors, in the present application a value of $OD_{610}=4$ translates, roughly, into a biomass density of 1 g/L.

According to the invention the culture of the methanogenic microorganisms can be guided or led into a high density culture with an $OD_{610}$ of at least 14, but preferably above 20, further also above 30, further above 40 and even up to 120 or 200 by supplying sufficient nutrient to the culture and simultaneously removing free or metabolic water from the culture. The method of the present invention can thus be suitably performed in culture of one or more strains of methanogenic microorganism, having throughout the various developmental stages a measurable $OD_{610}$ between 60-200; further an $OD_{610}$ between 14-120; further an $OD_{610}$ between 20-120; further an $OD_{610}$ between 30-120; further an $OD_{610}$ between 40-120; further an $OD_{610}$ between 50-120; further an $OD_{610}$ between 50-100; further an $OD_{610}$ between 14-80; further an $OD_{610}$ between 20-80; further an $OD_{610}$ between 30-80; further an $OD_{610}$ between 40-80; further an $OD_{610}$ between 20-80; further an $OD_{610}$ between 30-40; further an $OD_{610}$ between 40-60; further an $OD_{610}$ between 20-40.

A high optical density corresponding to a high number of cells is obtained into the growth phase and maintained by keeping the members of the culture in the bioreactor across the entire stages of their lives to their terminal stage, so that the remains of the inactive cellular bodies may provide nutrients to the active members of the culture.

Additionally, according to the present invention is that the culture of the methanogenic microorganisms can be guided or led into a density culture with an $OD_{610}$ of at least 0.04 or at least 0.1, but preferably above 0.3, further also above 0.4, further above 0.5 and even up to 0.6, 0.8, 1.0, 1.5, 2.0 or 2.5 by supplying sufficient nutrient to the culture and simultaneously removing free or metabolic water from the culture. The method of the present invention can thus be suitably performed in culture of one or more strains of methanogenic microorganism, having throughout the various developmental stages a measurable $OD_{610}$ between 0.1-2.5; further an between 0.3-2.5; further an $OD_{610}$ between 0.4-2.5; further an $OD_{610}$ between 0.5-2.5; further an $OD_{610}$ between 0.6-2.5; further an $OD_{610}$ between 0.1-2.0; further an $OD_{610}$ between 0.1-1.5; further an $OD_{610}$ between 0.1-0.8, further an $OD_{610}$ between 0.1-0.7; further an $OD_{610}$ between 0.1-0.6.

According to another embodiment of the present invention the sulfur source is selected from the group consisting of hydrogen sulfide, $Na_2S$, L-cysteine, elemental sulfur or sulphate or combinations of the aforementioned.

According to another embodiment of the present invention the method further comprises a source of a reductive element in the culture medium selected from the group consisting of hydrogen, hydrogen sulfide, the sulfur source, formic acid, carbon monoxide, reduced metals, sugars, acetate, cathodic electrodes or combinations of the aforementioned.

The sulfur source can also act as a reductive element. $Na_2S$ will be applied when the ORP a suboptimal value of above −250 mV, caused by e.g. an oxygen diffusion.

According to another embodiment of the present invention the at least one inorganic carbon source comprises electron equivalents and is selected from the group consisting of $CO_2$ gas, sodium carbonate, potassium carbonate and ammonium carbonate or combinations of the aforementioned.

According to an alternative embodiment of the present invention instead of or additionally to the at least one inorganic carbon source as disclosed above an organic carbon source may be used. The at least one organic carbon source may be selected from the group consisting of formate, acetate, methanol, methylamines and sugars or combinations of the aforementioned.

The at least one inorganic carbon source can be applied in a need-dependent and situation-dependent manner to face the particular needs of a culture of a certain microorganism strain specifically. In the prior art, the inorganic carbon source classically in the form of $CO_2$ gas is already given separately. According to the present invention the inorganic carbon source, e.g. in form of $CO_2$ may be applied as pure gas or alternatively delivered using the supply of industrial gases. Such industrial gases depending on their source may comprise very different gas compositions. They have primarily in common that they contain a relatively high amount of $CO_2$ in comparison to air. They may contain a normal (air-like) partial amount of oxygen and/or nitrogen, however, depending on their origin they may also be oxygen free. Additionally, they may contain substantial amounts of at least one of the following, particularly carbon monoxide, hydrogen and hydrogen sulfide, other sulphur compounds (sulfides, disulfides, thiols), siloxanes (organic silicon compounds), halogenated compounds, ammonia, and organochlorines, i.e. pesticides and other synthetic organic compounds with chlorinated aromatic molecules.

In some of the embodiments disclosed herein, the inorganic carbon source is supplied or regulated proportionate to the electron flow, wherein the inorganic carbon source comprising electron equivalents is supplied in at an electron equivalent to electron ratio.

According to an additional embodiment of the present invention the method further comprises the step of continuously controlling and regulating the flow of the inorganic carbon source comprising electron equivalents in dependence of the electron flow in an electron equivalent to electron ratio in a range of 1:20 to 1:1, or at 1:20, 1:18, 1:15, 1:12, 1:10, 1:9, 1:8, 1:7, 1:6, 1:5, 1:4, 1:3, 1:2 or 1:1, preferably in a range of 1:10 to 1:6, more preferably at 1:8 and the flow of the inorganic carbon source, e.g. of $CO_2$ into the MEC may be measured.

According to a preferred embodiment of the present invention the at least one inorganic carbon source is $CO_2$ gas and the method further comprises the step of continuously controlling and regulating the $CO_2$ flow to receive a $CO_2$:

electron ratio in a range of 1:20 to 1:1, or at 1:20, 1:18, 1:15, 1:12, 1:10, 1:9, 1:8, 1:7, 1:6, 1:5, 1:4, 1:3, 1:2 or 1:1, preferably in a range of 1:10 to 1:6 more preferably at 1:8. A current of 100 mA is equal to a $CO_2$: electron ratio of 1:4 with a $CO_2$ flow of 0.2 mL/min. Techniques and means how to measure the current are well known by the artisan, e.g., by mean of potentiostatic control in a 3-electrode system or using a power source with a 2-electrode system.

The inventors of the present invention have found that the controlling and regulating of the flow of the inorganic carbon source (e.g. the $CO_2$ flow) by a separate supply regime in dependence of the electron flow under such ratios will provide beneficial flexibility in terms of process operation with respect to maximizing of the methanogenesis.

According to a preferred additional embodiment the at least one inorganic carbon source is $CO_2$ and methane or a methane enriched gas composition is collected.

According to a further embodiment the at least one synthesis product different from methane or different from the methane enriched gas composition is selected from the group consisting of geraniol, vitamin A, cholesterol, carotenoids, and natural rubber.

According to an embodiment of the present invention the method further comprises the step of setting an initial pH value to be at a given value of pH 6 to 11, of pH 7 to 10 or at pH 8 and subsequent continuously controlling and regulating, i.e. stabilizing the pH value.

According to an embodiment of the present invention the separated nutrient supply system (nitrogen source and/or sulfur source); (nitrogen source, sulfur source, inorganic carbon source) may be applied to regulate an initial set pH value to be at a given value of pH 6.0 to 7.5 to promote cell division and cell growth or to regulate an initial set pH value to be at a given value of pH 7.5 to 9.0 to promote $CO_2$ capturing and thus $CH_4/CO_2$ conversion. The separated feeding supply beneficially also allows for a situation-dependent shift between such pH values of above, thus promoting cell growth and $CH_4/CO_2$ conversion as needed.

According to an embodiment of the present invention the step of controlling and regulating the pH value continuously to be kept at a given different value is done by dosing suitable amounts of a base and/or an acid, e.g. NaOH/HCl or $NH_4OH$/HCl to the culture.

Alternatively, when a decreased current lower than the desired range is detected, a responsive step comprises optionally (a) decreasing the supply of inorganic carbon source (e.g. $CO_2$ flow) or (b) pulsing additional fresh culture medium (e.g. separated culture medium) into the cathode chamber to increase salinity and therefore current production. As another example, when the pH decreases below the desired range, the nitrogen source supply (when delivered as a buffer form) may be temporarily increased in response. When the pH increases, acid may be added as a responsive step. As yet a further example, when the ORP increases above the desired range, the sulfur source supply may be temporarily increased in response, although the sulfur source may also increase pH.

In some aspects, when decreased efficiency of conversion is detected, a responsive step comprises increasing the supply of culture media, or nickel and/or the sulfur source (e.g. $Na_2S$); or alternatively increasing the supply of the nitrogen source.

The inventors have found that in general there is no need to supply externally $H_2$ to maintain overall methanation efficiency as e.g. the hydrolysis of water generates sufficient $H_2$ for the metabolism and maintenance of the culture of methanogenic microorganisms. However, if needed, e.g.

when there is a MEC misfunction, the external supply of $H_2$ in a discrete manner as an emergency treatment or just for assistance purposes to recover the culture could be appropriate.

Furthermore, according to an embodiment of the present invention a continuous external supply of $H_2$ is also possible. Thus, according to an additional embodiment of the present invention the method further comprises the step of contacting the methanogenic microorganisms with at least one feeding gas comprising $H_2$.

According to an embodiment of the present invention the used culture of methanogenic microorganisms resides floating within the culture medium or is at least partially bound to the cathode, e.g. as biofilm.

According to an embodiment of the present invention the organic inorganic carbon source is absent in the culture medium.

According to an embodiment of the present invention the methanogenic microorganisms are hydrogenotrophic and are selected from at least one of the group of Archaea or archaebacteria comprising of *Methanobacterium, Methanobrevibacter, Methanothermobacter, Methanococcus, Methanosarcina, Methanopyrus* or mixtures thereof.

As used herein, the term "hydrogenotrophic" refers to a microorganism capable of converting hydrogen to another compound as part of its metabolism. Classical hydrogenotrophic methanogenic microorganisms are capable of utilizing hydrogen ($H_2$) and an inorganic carbon source as $CO_2$ in the production of methane. However, according to an embodiment of the invention classical hydrogenotrophic methanogenic microorganisms according to the definitions as given above may be modified, e.g. by way of genetic modification to produce additionally other synthesis products as methane from $H_2$ and a carbon source, e.g. geraniol as described in Lyu et al., 2016.

The cathode according to the invention may be of a high surface to volume electrically conductive material. For example, the cathode may be made of an electrically conductive material, e.g. graphite. The cathode may be porous or non-porous at least at its surface. In particular, the cathode may be made from a reticulated vitreous carbon foam. According to certain reference examples, the pores of the cathode may be large enough (e.g., greater than 1-2 micrometers in minimum dimension) to accommodate living methanogenic microorganisms within the pores. The electrical conductivity of the cathode matrix is preferably at least two orders of magnitude greater than the ion conductivity of the aqueous electrolytic medium contained within its pores. The role of the cathode is to supply electrons to the microorganisms while minimizing side-reactions and minimizing energy loss.

SHORT DESCRIPTION OF THE FIGURES

FIG. 1: MEC scheme for different possible ways of methane production in the process of bio-electromethanation. Anode (indicated by A) and bio-cathode (indicated by C) chambers are separated by an ionic exchange membrane (PEM) (indicated by B). Flow of electrons is indicated by "e-" and associated arrows indicate the direction of the flow. Ean, Ecat, Ecell are the potentials of the anode, cathode and the MEC respectively. The difference between the two electrode potentials equals the cell potential: Ecell=Ecathode−Eanode. NHE: Normal Hydrogen Electrode. D indicates a methanogen; E and G indicate indirect electron transfer mechanisms; F indicates direct electron transfer mechanism; H and I indicate the chemical reactions for methane production under indirect and direct electron transfer mechanisms respectively. L indicates the chemical reaction for water oxidation at the anode. J and K indicate redox mediators.

FIG. 2: General overview on the MEC bio-electromethanogenesis process using a separate media supply system. The strain media requirements are supplied through a separate feeding system (indicated by three separated compartments) to allow for separated and independent nutrient supply. This system provides the versatility to act specifically on the potential different process scenarios. Legend: 1—Micro gas chromatography; 2—Outproduct gas; 3—Feeding system (separated media supply system); 4—Pump; 5—Inorganic carbon source; 6—MEC (left side: anode; right side: cathode) and 7—Power source and/or potentiostat.

FIG. 3: Scheme on relations of variables that interact bi-directionally with the sulfur source and the nitrogen source (theory of the inventors). Legend: 1—Energy density (electrons); 2—Hydrogen coulombic efficiency; 3—Hydrogen production rate; 4—Carbon dioxide flow required ($CO_2$); 5—ORP; 6—pH; 7—Conductivity; 8—Methane production rate (methanation) and 9—Cell density (optical density, OD); A indicates the nitrogen source and B the sulfur source.

Figure 4:
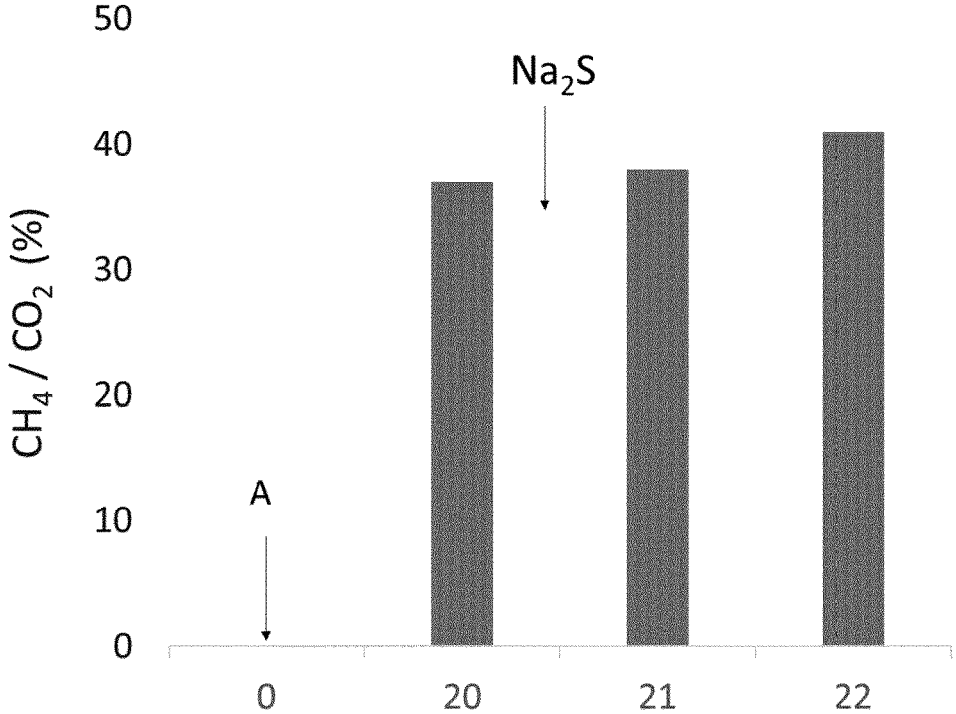

FIG. 4: Discrete supply of a punctual sulfur source pulse ($Na_2S$; 1 ml, 100 g/L) results in a fast increase in the conversion of $CO_2$ to $CH_4$. Legend: X axis indicates time (hours) after biocatalyst inoculation; Y axis indicates $CH_4$/$CO_2$ conversion in %; A indicates reactor inoculation.

Figure 5:
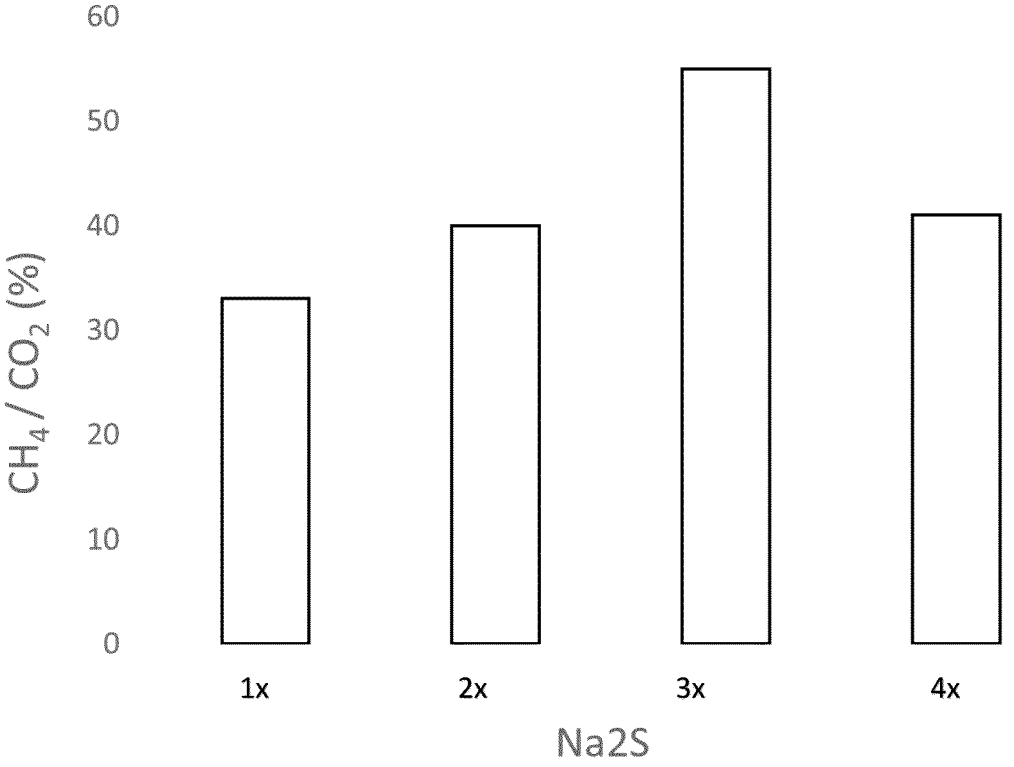

FIG. 5: Increase of the initial concentration of the sulfur source ($Na_2S$, "sulfide feeding") results in a fast and concentration dependent increase of the conversion of $CO_2$ to $CH_4$ (short term experiment). Legend: X axis indicates sulfur feeding at 4 different concentrations (1X-2X-3X and 4X); Y axis indicates $CH_4$/$CO_2$ conversion in %.

Figure 6:
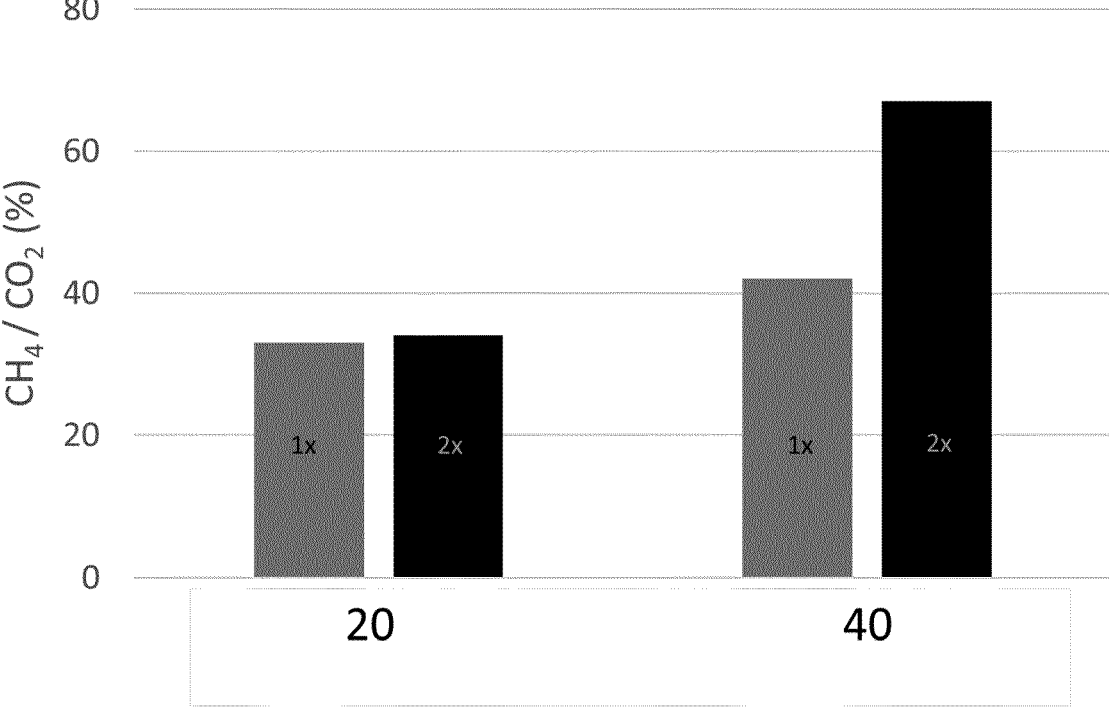

FIG. 6: Doubling the initial concentration of the sulfur source ($Na_2S$) results in an increase in the conversion of $CO_2$ to $CH_4$ over time (long term experiment). The initial concentration of $Na_2S$ is supplied at time 0, i.e., just right before the strain inoculation. Periodic $Na_2S$ (each 4 hours) was applied in both experiments maintaining the relation in the $Na_2S$ concentration applied, i.e., doubling it in one of the experiments regarding the other. Legend: X axis indicates time (hours) after biocatalyst inoculation in hours after sulfur feeding at 2 different concentrations (1X-2X); Y axis indicates $CH_4$/$CO_2$ conversion in %.

FIG. 7: Flow chart showing how a nitrogen and/or sulfur pulse (discrete supply) in the culture medium of a MEC influences parameters of the methanation process of an inoculated methanogen: Legend: 1—Pulse of nitrogen and/or sulfur source; 2—Increased conductivity at the cathode chamber; 3—Effect on pH and ORP; 4—Increased current production; 5—Increased hydrogen production; 6—Increased $CO_2$ inflow (under operation control); 7—Effect on $CH_4$/$CO_2$ conversion rate (increases); 8—Increased volumetric methane production; 9—Effect on cell density (increased OD). The $CO_2$ flow is adapted according to the current in order to establish the desired $CO_2$: electron ratio.

FIG. 8: The supply of two subsequent sulfur source pulses ($Na_2S$; indicated by arrow heads) results in a fast increase in the conversion of $CO_2$ to $CH_4$, while physical-chemical parameters do not change notably. Legend: X axis indicates time (hours) after inoculation; Y left axis indicates $CH_4$/$CO_2$ conversion in %; Y right axis indicates pH, ORP, and conductivity (σ (mS/cm)) respectively.

Figure 9:
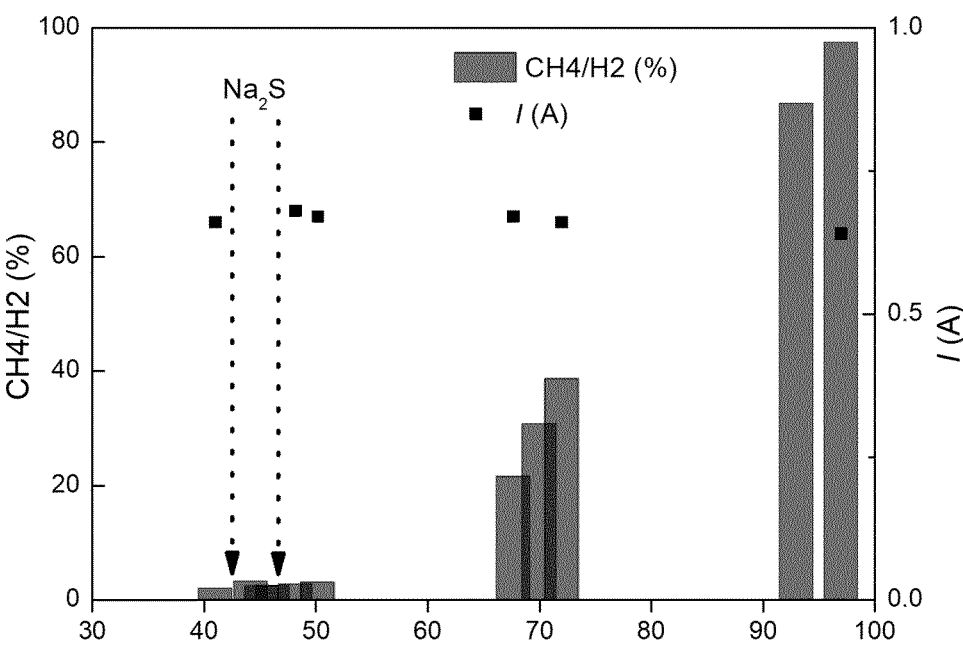

FIG. 9: The supply of two subsequent sulfur source pulses ($Na_2S$; indicated by arrow heads) results in a fast increase in the utilization of $H_2$ to reduce $CO_2$ to $CH_4$ (cf. columns), while the current production stays stable. Legend: X axis indicates time (hours) after biocatalyst inoculation; Y left axis indicates $CH_4$/$H_2$ conversion in %; Y right axis indicates current production in amperes (I (A); cf. squares).

Figure 10:
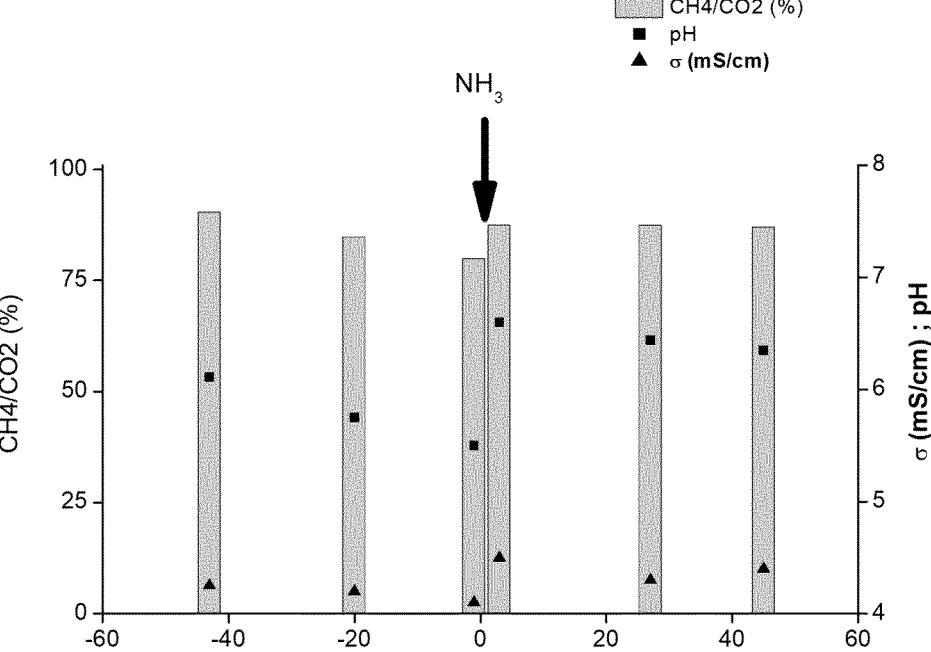

FIG. 10: A punctual supply of ammonia (nitrogen source) results in a fast increase in the conversion of $CO_2$ to $CH_4$. The increase of $CO_2$ conversion to $CH_4$ is limited for the $H_2$ availability at the cathode chamber. Legend: X axis indicates time (hours) before (negative) and after (positive) the ammonia pulse; Y left axis indicates $CH_4$/$CO_2$ conversion in % (cf. columns); Y right axis indicates conductivity (σ (mS/cm), cf. triangle) and pH (cf. squares).

Figure 11:
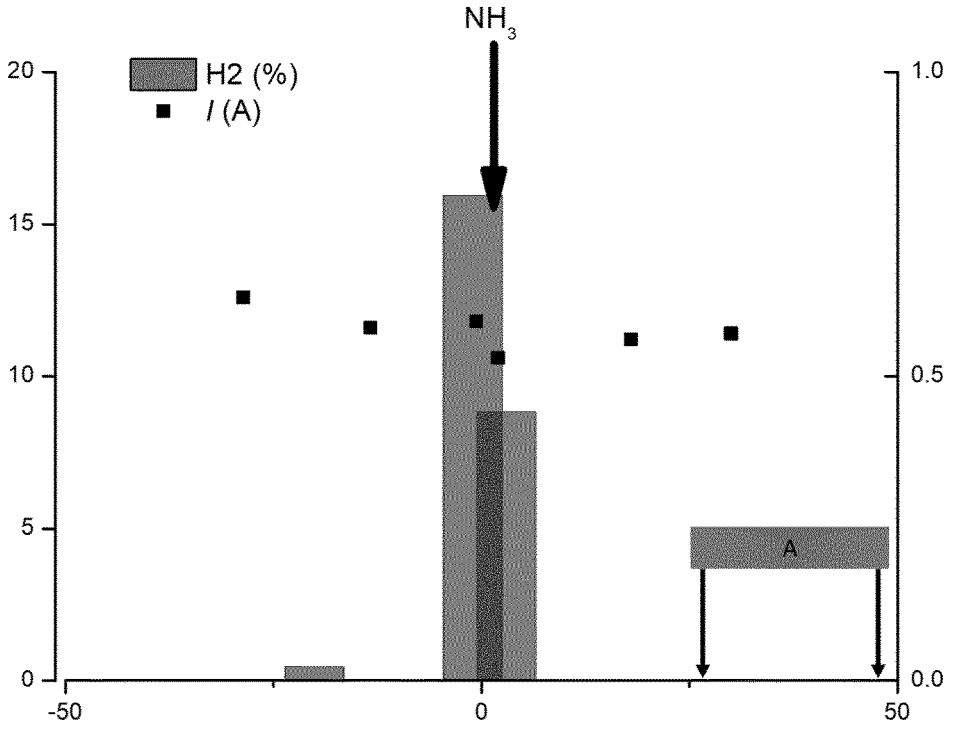

FIG. 11: The supply of ammonia (nitrogen source) results in a fast decrease of $H_2$ in the system while the current production stays stable. Legend: X axis indicates time (hours) before (negative) and after (positive) the ammonia pulse; Y left axis indicates $H_2$ at the product gas in % (cf. columns); Y right axis indicates current production in amperes (cf. squares); A indicates two outgas composition measurements where $H_2$ is totally depleted.

Figure 12:
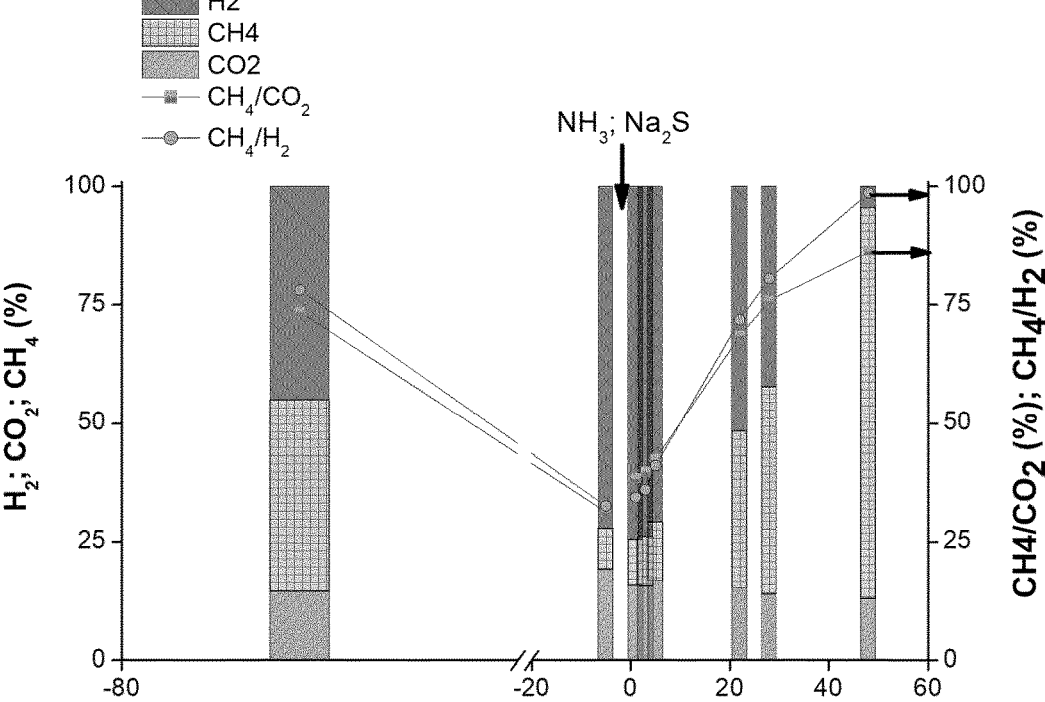

FIG. 12: The simultaneous supply of a sulfur source ($Na_2S$) and nitrogen source ($NH_3$) pulse results in a fast increase in the utilization of $H_2$ and $CO_2$ to produce methane ($CH_4$), increasing over 50% the conversion percentage of these 2 reactants to $CH_4$ in 24 hours. Legend: X axis indicates time (hours) before (negative) and after (positive) the simultaneous supply of ammonia and sulfur; Y left axis indicates $H_2$, $CO_2$ and $CH_4$ at the product gas in %; Y right axis indicates $CH_4$/$CO_2$ and $CH_4$/$H_2$ conversion in %.

EXAMPLES

The following examples illustrate viable ways of carrying out the described method as intended, without the intent of limiting the invention to said examples.

General Experimental Set-Up

The procedure of the general experimental set-up (MEC start-up) was as follows:

Add distill water at the anode and cathode circuit until the anode and cathode reservoir are fill up totally. Preferably, add 250 mL of distill water at the anode and cathode reservoir, each. Close the recirculating circuit and recirculate with the pump. At both reservoirs should be 100 mL left after filling up both the recirculating system and the MEC chambers (cathode and anode chamber). Otherwise level the reservoirs to 100 mL;

Heating system on (heat applied directly to the anode and cathode reservoirs (independently));

minutes purging the catholyte with argon: Purge in the argon into one of the inlet fitting of the catholyte recirculating system to create an anaerobic environment;

When the temperature is correct (ca. 65° C.) at the reservoirs, power on (a power source established a potential different between anode and cathode to drive the reactions);

Add all chemicals/media to the catholyte at the cathode reservoir/compartment. Adding the chemicals after the argon purging will avoid that the overpressure created under the purging phase supports chemical migration processes, preferably liquid migration processes from the anode to the cathode or vice versa. Na$_2$S has been already tested as sulfur source for optimizing methanogenesis;

Allow 30 minutes of equilibration after the chemical addition;

Make annotations in volume changes from the anode and cathode reservoir. Correct volume deviation due to liquid/ion migration processes if needed;

Strain inoculation: Inoculate with OD$_{610}$ 0.5 to 2, preferably 1.8;

CO$_2$ flow goes into at the cathode chamber. The flow will be regulated regarding the electron flow provided through the cathode (ratio 1 molecule of CO$_2$ to 12 electrons). This relation assures enough electron density to reduce the specific CO$_2$ flow;

Gas Chromatography (GC): H$_2$, CO$_2$, CH$_4$ and H$_2$ gas content will be determined with high periodicity (1 to 150 times), establishing the gas quality of the process;

Coulombic efficiency (CE) measurements should be taken with high periodicity (1 to 150 times). For that the output gas, i.e. gas that leaves the system should be harvested during a fixed time.

To make this calculation the gas volume and the electrical charge per unit of time must be registered. CE measurements should be a key parameter to evaluate the quality of our ratio CO$_2$ to electrons;

Periodically measure optical density (OD$_{610}$), pH, ORP and conductivity;

Periodically supply media if needed to compensate the dilution factor due to the metabolic water production;

Supply nitrogen source, when nitrogen source concentrations lower than 100 mg/L are reached;

Supply Na$_2$S on demand to maintain the ORP ideally below −350 mV.

Example 1: a Punctual Pulse of the Sulfur Source Results in a Fast Percentage Increase of the CO$_2$/CH$_4$ Conversion The experimental procedure was as follows:

Initially adding 5 mL Na$_2$S 0.758 M (100 g/L) and 6.5 mL NH$_4$Cl 4.8 M (no feeding of ammonia after the initial dose) to the catholyte, reaching a final volume of 250 mL Dosing each 4 hours (1 mL): 0.151 M Na$_2$S (20 g/L), starting at time point 4 hours after inoculation Inoculating the MEC with *Methanothermobacter thermautotrophicus* strain UC 120910 (ECH100 or ECH0100), a methanogenic microorganism (content of 10 mL culture bottle, OD$_{610}$45)

Setting initial CO$_2$ flow at 1 mL/min

Cathode: graphite cathode

Results

A discrete punctual pulse of Na$_2$S (1 mL 0.758 M (100 g/L)) resulted in a noticeable fast increase of the percentage CO$_2$ to CH$_4$ conversion. Already 1 h after the pulse there was an increase of 1% of the percentage CO$_2$ to CH$_4$ conversion detected towards the reference conversion, which was 37% at 20 h after MEC inoculation. Remarkedly, only one hours later, i.e., two hours after the pulse of Na$_2$S the percentage conversion increased 3% in relation to the reference at 20 h after MEC inoculation (cf. FIG. 4).

Example 2: Increasing the Initial Sulfur Source Concentration (Na$_2$S) LED to a Sulfur Source Concentration Dependent Increase of the CO$_2$ to CH$_4$ Conversion in the First 24 Hours (Short Term Experimentation)

To test the influence of the initial sulfur source concentration (Na$_2$S) on the percentage CO$_2$ to CH$_4$ conversion example 2 was performed.

The experimental procedure was as follows:

Inoculating the MEC with *Methanothermobacter thermautotrophicus* strain UC 120910 (ECH100 or ECH0100) a methanogenic microorganisms (content of 10 mL culture bottle, OD$_{610}$45, preferably final OD$_{610}$ 1.8)

Initial ammonia concentration 120 mM (no feeding of ammonia after the initial dose); E.g., initially adding 6.5 mL NH$_4$Cl (no feeding of ammonia after the initial dose) reaching a final volume of 250 mL CO$_2$ flow regulated comprising electron equivalents in dependence of the electron flow in an electron equivalent to electron ratio in a range of 1:20 to 1:1, more preferably at 1:10. Preferably, setting initial CO$_2$ flow at 1 mL/min Cathode: graphite cathode Feeding Initial sulfur source concentration, so 1× (7.5 mM), 2× (15 mM), 3× (22.5 mM) and 4× (30 mM) Na 2 S are the initial sulfur concentration of the experiment.

Measuring 24 h after setting the sulfur source concentration

Results

There was a significant Na$_2$S concentration dependent increase of the percentage CO$_2$ to CH$_4$ conversion, when increasing the Na$_2$S concentration from 1× to 2× and 3X. A 4× Na$_2$S concentration showed still an increase on above a CO$_2$ to CH$_4$ conversion level of 40% as compared to the level when applying a 1× Na$_2$S concentration. Moreover, also the pH and the current increased concentration dependently (cf. FIG. 5). The measured ratio of the projected electrode area [m$^2$]:sulfur source concentration [mol/L] in the culture medium is given in Table 1.

In more detail, the following values of the following parameters were detected:

1× Na$_2$S: pH 7.3; current: 213 mA
2× Na$_2$S: pH 7.6; current: 240 mA
3× Na$_2$S: pH 7.8; current: 280 mA
4× Na$_2$S: pH 8.1; current: 320 mA

TABLE 1

Added amount of the 100 g/L of Na$_2$S (pulse) and the resulting molarity after the pulse in the cell culture medium for all Examples (total volume of the cell culture medium = 250 ml) and measured ratio of the projected electrode area [m$^2$]: sulfur source concentration [mol/L] in the culture medium.

| Pulse parameters | Resulting molarity in the cell culture medium after the pulse | Measured ratio of the projected electrode area [m$^2$]: sulfur source concentration [mol/L] in the culture medium |
|---|---|---|
| Initial pulse of 2.5 mL of 100 g/L Na2S trihydrate solution (molecular weight 132 g); 1X Na$_2$S | 7.5 mM | 1:0.8 |
| Initial pulse of 5 ml of 100 g/L Na2S trihydrate solution | 15 mM | 1:1.5 |

TABLE 1-continued

Added amount of the 100 g/L of $Na_2S$ (pulse) and the resulting
molarity after the pulse in the cell culture medium for all
Examples (total volume of the cell culture medium = 250 ml) and
measured ratio of the projected electrode area [$m^2$]: sulfur
source concentration [mol/L] in the
culture medium.

| Pulse parameters | Resulting molarity in the cell culture medium after the pulse | Measured ratio of the projected electrode area [$m^2$]: sulfur source concentration [mol/L] in the culture medium |
| --- | --- | --- |
| (molecular weight 132 g); 2X $Na_2S$ Initial pulse of 7.5 mL of 100 g/L Na2S trihydrate solution (molecular weight 132 g); 3X $Na_2S$ | 22.5 mM | 1:2.2 |
| Initial pulse of 10 mL of 100 g/L Na2S trihydrate solution (molecular weight 132 g); 4X $Na_2S$ | 30 mM | 1:3 |

Example 3: Doubling of the Sulfur Source Concentration Results in a Significant Increase of the $CO_2$ to $CH_4$ Conversion Over Time (Long Term Experimentation)

To further investigate the influence of the initial sulfur source concentration ($Na_2S$) on the percentage $CO_2$ to $CH_4$ conversion on a long time scale basis the following experiment was performed using 1× (7.5 mM) and 2× (15 mM) $Na_2S$ concentrations.

The experimental procedure was as follows:
Inoculating the MEC with *Methanothermobacter thermautotrophicus* strain UC 120910 (ECH100 or ECH0100) a methanogenic microorganisms (content of 10 mL culture bottle, $OD_{610}$ 45)
Initial ammonia concentration 120 mM (no feeding of ammonia after the initial dose); e.g.: Initially adding 6.5 mL $NH_4Cl$ (no feeding of ammonia after the initial dose) reaching a final volume of 250 mL
$CO_2$ flow regulated comprising electron equivalents in dependence of the electron flow in an electron equivalent to electron ratio in a range of 1:20 to 1:1, more preferably at 1:10. Preferably, setting initial $CO_2$ flow at 1 mL/min
Cathode: graphite cathode
Feeding Initial sulfur source concentration, so 1× (7.5 mM), 2× $Na_2S$ (15 mM)
Measuring points: 20 and 40 hours after setting the sulfur source concentration.
Results
Notably, there was a significant high increase of the percentage $CO_2$ to $CH_4$ conversion in a $Na_2S$ concentration dependent manner over time, when increasing the initial $Na_2S$ concentration from 1× to 2×. 40 h after MEC inoculation the $CO_2$ to $CH_4$ conversion was more than 25% higher in the 2× $Na_2S$ concentration approach as compared to the 1× $Na_2S$ concentration approach. Similarly, to the experiment in the previous examples, also the pH and the current increased concentration dependently (cf. FIG. 6).
In more detail, the following values of the following parameters were detected 40 h after MEC inoculation:
1× $Na_2S$: pH 7.2; current: 220 mA; salinity: Anode 5.8 mS·cm-1, cathode 15.7 mS·cm-1
2× $Na_2S$: pH 7.9; current: 290 mA; salinity: Anode 7.5 mS·cm-1, cathode 17 mS·cm-1.

Example 4: A Punctual Supply of the Sulfur Source Results in a Fast Percentage Increase of the $CO_2$ and $H_2$ Conversion to $CH_4$ The experimental procedure was as follows:
Inoculating the MEC with *Methanothermobacter thermautotrophicus* strain UC 120910 (ECH100 or ECH0100) a methanogenic microorganism (final concentration $OD_{610}$ 1.8)
Initial $Na_2S$ concentration 0.5 mM (no feeding of $Na_2S$ after the initial dose)
flow regulated comprising electron equivalents in dependence of the electron flow in an electron equivalent to electron ratio in a range of 1:20 to 1:1, more preferably at 1:10.
Cathode: graphite cathode
Results
Two subsequence (separated for 5 hours) discrete pulses of $Na_2S$ (with a total increase of 1.2 mM $Na_2S$ concentration) resulted in a noticeable fast increase of the percentage of $CO_2$ to $CH_4$ conversion. 25 h after the double pulse, the $CO_2$ to $CH_4$ conversion beneficially increases over 35% and after 50 hours, even more pronounced, i.e., over 87% compared to the pre-pulse conversion (cf. FIG. 8). Physical-chemical parameters did not change notably. Parallel results were obtained in relation to the $H_2$ utilization to produce methane (cf. FIG. 9). Notably, here, an increase over 90% in 50 hours under a very stable current production was detected.

Example 5: A Punctual Supply of the Nitrogen Source Results in a Fast Percentage Increase of the $CO_2$ and $H_2$ Conversion to $CH_4$ The experimental procedure was as follows:
Inoculating the MEC with *Methanothermobacter thermautotrophicus* strain UC 120910 (ECH100 or ECH0100) (final concentration $OD_{610}$ 1.8)
Initial ammonium chloride ($NH_4CL$) concentration 16 mM (no regular feeding after initial dose)
$CO_2$ flow regulated comprising electron equivalents in dependence of the electron flow in an electron equivalent to electron ratio in a range of 1:20 to 1:1, more preferably at 1:10.
Cathode: graphite cathode
Results
A discrete punctual pulse of ammonium hydroxide ($NH_4OH$) (with a total increase of 7.5 mM concentration in the catholyte) resulted in a markedly 7% increase on the $CO_2$ to $CH_4$ conversion within only one hour (cf. FIG. 10). While conductivity showed no drastic change, the pH varied over 1 unit after the pulse. Interestingly, the increase of $CO_2$ conversion to $CH_4$ was found to be limited by the $H_2$ availability in the system. It totally depleted after the ammonium hydroxide pulse (cf. FIG. 11). The ammonium hydroxide triggered an OD increase over 2.5-fold within 50 hours.

Example 6: A Simultaneous Pulse of Nitrogen and Sulfur Sources Results in a Fast Percentage Increase of the $CO_2$ and $H_2$ Conversion to $CH_4$ To further investigate the influence of the nutrient punctual supply the following experiment was performed. Pulsing simultaneously (overlapping time points, i.e., in a simultaneous manner) ammonium hydroxide $NH_4OH$ (establishing a 7.5 mM increase of the total concentration of this compound in the catholyte) and Na₂S (establishing a 1.2 mM increase of the total concentration of this compound in the catholyte)

The experimental procedure was as follows:

Inoculating the MEC with *Methanothermobacter thermautotrophicus* strain UC 120910 (ECH100 or ECH0100) (final concentration $OD_{610}$ 1.8)

CO₂ flow regulated comprising electron equivalents in dependence of the electron flow in an electron equivalent to electron ratio in a range of 1:20 to 1:1, more preferably at 1:10.

No regular feeding applied

Cathode: graphite cathode

Results

Notably and very promisingly, there was a significant beneficial synergistic increase (over 50%) of the percentage $CO_2$ and $H_2$ conversion to $CH_4$ within 24 hours after punctually pulsing ammonium hydroxide (a total increase of 7.5 mM in the catholyte increasing) and Na₂S (establishing a 1.2 mM increase of the total concentration of this compound in the catholyte) in a simultaneous manner (cf. FIG. 12). 48 hours after the pulse the $H_2$ was almost depleted, with less than 5% in the product gas.

REFERENCES

Lyu Z, Jain R, Smith P, Fetchko T, Yan Y, Whitman W B (2016) Engineering the autotroph for geraniol production. ACS Synth Biol 5:577-581.

The invention claimed is:

1. A method to produce methane during the methane production phase or at least one other synthesis product by methanogenic microorganisms in a microbial electrolysis cell (MEC), the method comprising the steps:
    i. providing a MEC, comprising an anode, a cathode, and a culture of methanogenic microorganisms in a suitable liquid aqueous electrolytic culture medium;
    ii. culturing the methanogenic microorganisms in a continuous process;
    iii. supplying electrons from the anode to the cathode of the MEC and contacting the methanogenic microorganisms with said electrons;
    iv. contacting the methanogenic microorganisms with at least one inorganic carbon source;
    v. contacting the methanogenic microorganisms with a sulfur source, or with a nitrogen source and a sulfur source, by separately supplying at least one of the nitrogen source and the sulfur source in a discrete or a continuous manner into the culture medium, thereby continuously controlling and regulating the concentration of the supplement source in the culture medium to maintain the nitrogen source concentration in the culture medium to be at a given amount of 0.005 to 0.2 M, or the sulfur source concentration in the culture medium to be at a given amount of 0.1 to 100 mM;
    vi. collecting methane, a methane enriched gas composition, or at least one other synthesis product from the MEC.

2. The method according to claim 1, wherein the MEC comprises at least:
    (a) a first chamber containing the cathode and the culture of the methanogenic microorganism in the culture medium; and
    (b) a second chamber containing at least the anode.

3. The method according to claim 1, wherein step v. further comprises:

that the nitrogen source concentration in the culture medium is maintained to be at a given amount of 0.02 to 0.2 M, or between 0.01 to 0.02 M or the sulfur source concentration in the culture medium is maintained to be at a given amount of 10 to 80 mM, or between 15 to 30 mM.

4. The method according to claim 1, wherein the sulfur source is supplied to maintain a ratio of a projected electrode area ($m^2$) to sulfur source concentration in the culture medium (mol/L) in the range of 1:0.001 to 1:0.1, 1:0.1 to 1:10, or 1:1.5 to 1:3.

5. The method according to claim 1, wherein step v. further comprises to continuously control and regulate the concentration of at least one other source of inorganic elements in the culture medium in their elemental form or in a form of any suitable non-toxic salt ions thereof selected from the group consisting of sodium, potassium, magnesium, calcium, iron, chloride, and phosphate by a separate supply in a continuous or discrete manner.

6. The method according to claim 1, wherein the step of culturing the methanogenic organisms further comprises:
    keeping the culture conditions anaerobic or facultatively anaerobic;
    keeping the temperatures in a range from 32° C. to 85° C.;
    carrying out the entire method or at least one step under atmospheric pressure conditions or under pressurized conditions with up to 16 or up to 420 bar;
    maintaining the methanogenic microorganism density at a range of 0.01-50 g/L, 0.025-0.625 g/L, 0.1-0.5 g/L, 3.5-30 g/L, 5-20 g/L or 5-10 g/L.

7. The method according to claim 1, wherein the nitrogen source is diatomic nitrogen ($N_2$), ammonia ($NH_3$), nitrate or nitrite salt ions, ammonium ($NH_4^+$) compounds.

8. The method according to claim 1, wherein the sulfur source is selected from the group consisting of hydrogen sulfide, Na₂S, L-cysteine, elemental sulfur, and sulphate, or a combination thereof.

9. The method according to claim 1, further comprising a source of a reductive element in the culture medium selected from the group consisting of hydrogen, hydrogen sulfide, the sulfur source, formic acid, carbon monoxide, reduced metals, sugars, acetate, and cathodic electrodes, or a combination thereof.

10. The method according to claim 1, wherein the at least one inorganic carbon source comprises electron equivalents and is selected from the group consisting of $CO_2$ gas, sodium carbonate, potassium carbonate, and ammonium carbonate, or a combination thereof.

11. The method according to claim 10, further comprising the step of continuously controlling and regulating the flow of the inorganic carbon source comprising electron equivalents in dependence of the electron flow in an electron equivalent to electron ratio in a range of 1:20 to 1:1.

12. The method according to claim 10, wherein the at least one inorganic carbon source is $CO_2$ gas.

13. The method according to claim 1, wherein the at least one inorganic carbon source is $CO_2$ and methane, or a methane enriched gas composition is collected.

14. The method according to claim 1, wherein the at least one other synthesis product selected from the group consisting of isoprene, geraniol, vitamin A, cholesterol, carotenoids, and natural rubber.

15. The method according to claim 1, further comprising the step of setting an initial pH value to be at a given value of pH 6 to 11, of pH 7 to 10, or at pH 8 and, subsequently, continuously controlling and regulating the pH value.

16. The method according to claim 1, further comprising the step of contacting the methanogenic microorganisms with at least one feeding gas comprising $H_2$.

17. The method according to claim 1, wherein the used culture of methanogenic microorganisms resides floating within the culture medium or is at least partially bound to the cathode.

18. The method according to claim 1, wherein the methanogenic microorganisms are hydrogenotrophic and are selected from at least one of the group of Archaea or archaebacteria consisting of *Methanobacterium, Methanobrevibacter, Methanothermobacter, Methanococcus, Methanosarcina*, and *Methanopyrus*, or mixtures thereof.

19. The method according to claim 1, further comprising (c) a proton permeable, gas impermeable barrier between the first chamber and the second chamber.

20. The method according to claim 1, wherein the nitrogen source or the sulfur source are supplied in a discrete manner.

21. The method according to claim 4, wherein the sulfur source is supplied to maintain a ratio of a projected electrode area ($m^2$) to sulfur source concentration in the culture medium (mol/L) in the range of 1:2 to 1:3 or 1:2 to 1:2.5.

22. The method according to claim 7, wherein the nitrogen source is in the form of $NH_4OH$, $NH_4Cl$, or combinations thereof.

23. The method according to claim 11, wherein the electron equivalent to electron ratio is from 1:10 to 1:6.

24. The method according to claim 23, wherein the electron equivalent to electron ratio is 1:8.

\* \* \* \* \*